United States Patent
Collier et al.

(10) Patent No.: US 11,061,039 B2
(45) Date of Patent: Jul. 13, 2021

(54) COMPOSITIONS AND METHODS FOR PURIFICATION AND DETECTION OF HDL AND APOA1

(71) Applicant: CLEVELAND HEARTLAB, INC., Cleveland, OH (US)

(72) Inventors: Timothy Collier, Cleveland, OH (US); Cory Bystrom, Beachwood, OH (US); Angela Higgins, Beachwood, OH (US)

(73) Assignee: Cleveland Heartlab, Inc., Cleveland, OH (US)

(*) Notice: Subject to any disclaimer, the term of this patent is extended or adjusted under 35 U.S.C. 154(b) by 0 days.

(21) Appl. No.: 16/208,739

(22) Filed: Dec. 4, 2018

(65) Prior Publication Data

US 2019/0250177 A1 Aug. 15, 2019

Related U.S. Application Data

(62) Division of application No. 14/713,046, filed on May 15, 2015, now Pat. No. 10,151,764.

(60) Provisional application No. 61/993,696, filed on May 15, 2014.

(51) Int. Cl.
  *G01N 33/483* (2006.01)
  *G01N 33/92* (2006.01)
  *G01N 1/34* (2006.01)
  *C07K 14/775* (2006.01)

(52) U.S. Cl.
  CPC .......... *G01N 33/92* (2013.01); *C07K 14/775* (2013.01); *G01N 1/34* (2013.01)

(58) Field of Classification Search
  None
  See application file for complete search history.

(56) References Cited

U.S. PATENT DOCUMENTS

| | | |
|---|---|---|
| 7,223,726 B2 | 5/2007 | Oda et al. |
| 7,838,631 B2 | 11/2010 | Yamashita et al. |
| 8,338,110 B2 | 12/2012 | Hazen et al. |
| 8,536,117 B2 | 9/2013 | Smith et al. |
| 2003/0181372 A1 | 9/2003 | Oda et al. |
| 2003/0212253 A1 | 11/2003 | Hammond et al. |
| 2006/0035858 A1 | 2/2006 | Geary et al. |
| 2012/0103072 A1 | 5/2012 | Kalantar-Zadeh et al. |
| 2013/0017556 A1 | 1/2013 | Prtichard, Jr. et al. |
| 2013/0071871 A1* | 3/2013 | Kaufman ........... G01N 33/6893 435/26 |
| 2013/0231461 A1 | 9/2013 | Adelman et al. |
| 2015/0331000 A1 | 5/2015 | Collier et al. |

FOREIGN PATENT DOCUMENTS

| | | |
|---|---|---|
| CN | 1114421 A | 1/1996 |
| CN | 1189378 A | 8/1998 |
| CN | 1699419 A | 11/2005 |
| CN | 1743455 A | 3/2006 |
| CN | 101319975 A | 12/2008 |
| EP | 2 009 447 A2 | 12/2008 |
| WO | WO83/04053 | 11/1983 |
| WO | WO93/06868 | 4/1993 |
| WO | WO94/08629 | 4/1994 |
| WO | WO94/09056 | 4/1994 |
| WO | WO96/26754 | 9/1996 |
| WO | WO 2006/138520 A2 | 12/2006 |
| WO | WO2015/175864 | 11/2015 |

OTHER PUBLICATIONS

Kees et al., Purification of His-Tagged Proteins by Immobilized Chelate Affinity Chromatography: The Benefits from the Use of Organic Solvent, Protein Expression and Purification 18, 2000, pp. 95-99. (Year: 2000).*
Office Action and Search Report dated Sep. 16, 2019, in CN 201580030344, English translations.
Harman et al., "Separation of the principal HDL subclasses by iodixanol gradient ultracentrifugation," Atherosclerosis, Sep. 2007, 194(1):283-284.
Bielicki et al., Apolipoprotein A-I(Milano) and apolipoprotein A-I(Paris) exhibit an antioxidant activity distinct from that of wild-type apolipoprotein A-I, Biochemistry. Feb. 12, 2002;41(6):2089-96.
Contois et al., Immunoprecipitation of apolipoprotein B-containing lipoproteins for isolation of HDL particles. Clinica Chimica Acta 2014; 436:348-350.
Eckerson et al. The human serum paraoxonase/arylesterase polymorphism, Am J Hum Genet. Nov. 1983;35(6):1126-38.
Fiddyment et al., Expression and purification of recombinant apolipoprotein A-I Zaragoza (L144R) and formation of reconstituted HDL particles, Protein Expr Purif. Nov. 2011;80(1):110-6.
Florvall et al., Apolipoprotein A1 is a stronger prognostic marker than are HDL and LDL cholesterol for cardiovascular disease and mortality in elderly men, J Gerontol A Biol Sci Med Sci. Dec. 2006;61(12):1262-6.
Frank et al., Apolipoprotein A-I: structure-function relationships, J Lipid Res. Jun. 2000;41(6):853-72.
Genbank Accession No. NM_000039, retrieved Jun. 20, 2016, 4 pages.
Genbank Accession No. NP_001634, retrieved Jun. 20, 2016, 3 pages.
Harman et al., Separation of the principal HDL subclasses by iodixanol ultracetrifugation. J Lipid Res 2013; 54:2273-2281.

(Continued)

*Primary Examiner* — Gary Counts
(74) *Attorney, Agent, or Firm* — Foley & Lardner LLP

(57) ABSTRACT

The present invention provides methods, kits, and compositions for purifying HDL molecules from a sample (e.g., blood sample) using HDL tagging molecules comprising an HDL lipophilic core binding peptide (e.g., portion of ApoA1) and an affinity tag. The present invention also provides methods, kits, and compositions for detecting non-fragmented ApoA1 with mass spectrometry. The present invention further provides methods, kits, and compositions for tagging HDL molecules in a sample with detectably labeled ApoA1 molecules such that the ratio of detectably labeled ApoA1 molecules to native ApoA1 proteins may be determined.

9 Claims, 15 Drawing Sheets

Specification includes a Sequence Listing.

(56) References Cited

OTHER PUBLICATIONS

Pankhurst et al., Characterization of specifically oxidized apolipoproteins in mildly oxidized high density lipoprotein, J Lipid Res. Feb. 2003;44(2):349-55.

Shao et al, Oxidation of apolipoprotein A-I by myeloperoxidase impairs the initial interactions with ABCA1 required for signaling and cholesterol export, J Lipid Res. Jul. 2010;51(7):1849-58.

Shao et al., Myeloperoxidase: an oxidative pathway for generating dysfunctional high-density lipoprotein, Chem Res Toxicol. Mar. 15, 2010;23(3):447-54.

Tanaka, Evaluation of lipid-binding properties of the N-terminal helical segments in human apolipoprotein A-I using fragment peptides, J Pept Sci. Jan. 2009;15(1):36-42.

Tomalia et al. Starburst Dendrimers: Molecular-Level Controal of Size, Shape, Surface Chemistry, Topology, and Flexibility from Atoms to Macroscopic Matter, Angew. Chem. Int. Ed. Engl., 1990, 29:138-175.

Warnick et al., Evolution of methods for measurement of HDL-cholesterol: from ultracentrifugation to homogeneous assays, Clin Chem. Sep. 2001;47(9):1579-96.

Weisgraber et al. Apolipoprotein A-IMilano. Detection of normal A-I in affected subjects and evidence for a cysteine for arginine substitution in the variant A-I, J Biol Chem. Feb. 25, 1983;258(4):2508-13.

International Search Report and Written Opinion for PCT/US2015/030949, dated Sep. 14, 2015, 8 pages.

European Extended Search Report for EP15792711.2, dated Dec. 8, 2017, 11 pages.

Collier et al., "Rapid Affinity Enrichment of Human Apolipoprotein A-I Associated Lipoproteins for Proteome Analysis," J. Proteome Res., 2018, 17:1183-1193.

European Search Report dated Dec. 3, 2019 in EP 19191273.2.

Office Action dated Dec. 1, 2020 in EP 19191273.2.

Sato et al., "Critical role of ABCA1 transporter in sphingosine 1-phosphate release from astrocytes," Journal of Neurochemistry, 2007, 103:2610-2619.

\* cited by examiner

His-tag affinity preparation

UC preparation

1. Ladder
2. Serum (1:50dilution)
3. Ni-NTA HDL prep (10ul)
4. UC HDL prep (10ul)
5. ApoA1 (purified from humans, 5ug)

SEQUENCE LISTING

```
<160> NUMBER OF SEQ ID NOS: 1

<210> SEQ ID NO 1
<211> LENGTH: 243
<212> TYPE: PRT
<213> ORGANISM: Artificial sequence
<220> FEATURE:
<223> OTHER INFORMATION: Synthetic

<400> SEQUENCE: 1

Asp Glu Pro Pro Gln Ser Pro Trp Asp Arg Val Lys Asp Leu Ala Thr
1               5                   10                  15

Val Tyr Val Asp Val Leu Lys Asp Ser Gly Arg Asp Tyr Val Ser Gln
            20                  25                  30

Phe Glu Gly Ser Ala Leu Gly Lys Gln Leu Asn Leu Lys Leu Leu Asp
        35                  40                  45

Asn Trp Asp Ser Val Thr Ser Thr Phe Ser Lys Leu Arg Glu Gln Leu
    50                  55                  60

Gly Pro Val Thr Gln Glu Phe Trp Asp Asn Leu Glu Lys Glu Thr Glu
65                  70                  75                  80

Gly Leu Arg Gln Glu Met Ser Lys Asp Leu Glu Glu Val Lys Ala Lys
                85                  90                  95

Val Gln Pro Tyr Leu Asp Asp Phe Gln Lys Lys Trp Gln Glu Glu Met
            100                 105                 110

Glu Leu Tyr Arg Gln Lys Val Glu Pro Leu Arg Ala Glu Leu Gln Glu
        115                 120                 125

Gly Ala Arg Gln Lys Leu His Glu Leu Gln Glu Lys Leu Ser Pro Leu
```

```
                130                 135                 140
Gly Glu Glu Met Arg Asp Arg Ala Arg Ala His Val Asp Ala Leu Arg
145                 150                 155                 160

Thr His Leu Ala Pro Tyr Ser Asp Glu Leu Arg Gln Arg Leu Ala Ala
                165                 170                 175

Arg Leu Glu Ala Leu Lys Glu Asn Gly Gly Ala Arg Leu Ala Glu Tyr
                180                 185                 190

His Ala Lys Ala Thr Glu His Leu Ser Thr Leu Ser Glu Lys Ala Lys
                195                 200                 205

Pro Ala Leu Glu Asp Leu Arg Gln Gly Leu Leu Pro Val Leu Glu Ser
                210                 215                 220

Phe Lys Val Ser Phe Leu Ser Ala Leu Glu Glu Tyr Thr Lys Lys Leu
225                 230                 235                 240

Asn Thr Gln
```

COMPOSITIONS AND METHODS FOR PURIFICATION AND DETECTION OF HDL AND APOA1

The present application is a divisional of U.S. patent application Ser. No. 14/713,046, filed May 15, 2015, issued as U.S. Pat. No. 10,151,764, which claims priority to U.S. Provisional application No. 61/993,696 filed May 15, 2014, each of which is herein incorporated by reference.

FIELD OF THE INVENTION

The present invention provides methods, kits, and compositions for purifying HDL molecules from a sample (e.g., blood sample) using HDL tagging molecules comprising an HDL lipophilic core binding peptide (e.g., portion of ApoA1) and an affinity tag. The present invention also provides methods, kits, and compositions for detecting non-fragmented ApoA1 with mass spectrometry. The present invention further provides methods, kits, and compositions for tagging HDL molecules in a sample with detectably labeled ApoA1 molecules such that the ratio of detectably labeled ApoA1 molecules to native ApoA1 proteins may be determined.

BACKGROUND

Serum lipoproteins comprise a heterogeneous population of lipid-protein complexes that can be grouped into broad classes, very low (VLDL), low (LDL) and high (HDL) density, based on differences in particle density related to lipid and protein content. VLDL and LDL are composed of predominately lipid, while high density lipoproteins have a higher content of protein (about 50%). The density of LDL is between 1.006-1.063 g/ml while that of HDL and HDL-like particles is 1.063-1.21 g/ml. Classical methods to separate HDL from VLDL and LDL employ sequential density ultracentrifugation using potassium bromide salt solutions prepared with densities in the range of each lipoprotein class. One drawback of these methods for the preparation of purified HDL is that they require a minimum of two prolonged ultracentrifugation steps. The first step, which isolates VLDL and LDL from HDL, requires an 18 hour ultracentrifugation spin in d=1.063 g/ml KBr salt solution. The buoyant VLDL and LDL are concentrated in the upper layers of the salt gradient and can be easily removed leaving the less buoyant HDL along with other heavier proteins concentrated in the bottom layers. The HDL is then separated from other lipid-free serum proteins by performing a second ultracentrifugation step for 21 hours in d=1.21 g/ml KBr salt solution. The HDL is buoyant in this density salt solution thus at the end of the centrifugation, the upper layers of the gradient contains primarily HDL leaving other plasma proteins in the bottom fraction. This sequential density gradient ultracentrifugation procedure is the "gold standard" for isolation of HDL. However the prolonged time required for both ultracentrifugation steps and the need for multiple density adjustments clearly limits the throughput of the procedure.

SUMMARY OF THE INVENTION

The present invention provides methods, kits, and compositions for purifying HDL molecules from a sample (e.g., blood sample) using HDL tagging molecules comprising an HDL lipophilic core binding peptide (e.g., portion of ApoA1) and an affinity tag. In certain embodiments, such HDL purification is rapid (e.g., less than 1 hour) and allows a determination of at least one cardiovascular risk factor (e.g., cholesterol level, oxidation status of ApoA1, etc.). The present invention also provides methods, kits, and compositions for detecting non-fragmented ApoA1. The present invention further provides methods, kits, and compositions for tagging HDL molecules in a sample with detectably labeled ApoA1 molecules such that the ratio of detectably labeled ApoA1 molecules to native ApoA1 proteins may be determined.

In some embodiments, provided here are methods of generating a purified sample comprising: a) mixing an initial sample (e.g., a sample that is or is not depleted in ApoB/LDL) containing a population of HDL molecules (e.g., mature HDL molecules) and non-HDL biomolecules with a population of HDL tagging molecules to generate a mixed sample, wherein the HDL molecules each comprise: i) an HDL lipophilic core and ii) a plurality of HDL lipoproteins, and wherein the HDL tagging molecules each comprise: i) an HDL lipophilic core binding peptide, and ii) an affinity tag; b) incubating the mixed sample such that at least some of the HDL tagging molecules bind to at least some of the HDL molecules thereby generating a population of tagged HDL molecules; and c) purifying at least a portion of the population of tagged HDL molecules away from the non-HDL biomolecules (and non-tagged HDL molecules) to generate a purified sample, wherein the purifying comprises contacting the mixed sample with a population of capture molecules that are specific for the affinity tag.

In certain embodiments, the HDL tagging molecules are added to the initial sample such that the ratio of tagged ApoA1 molecules to non-tagged ApoA1 molecules is about 1:10-10:1, 1:5-4:1, or about 1:3-3:1, or about 1:2-2:1; or about 1:1. In certain embodiments, the initial sample is a serum sample, and the amount of HDL tagging molecules added to the serum sample is about 0.1 mg-4 mg per ml of serum sample, or about 0.5 mg-2 mg per ml of serum sample, or about 1 mg per ml of serum sample.

In some embodiments, provided herein are compositions comprising: a) a population of HDL tagging molecules comprising: i) at least a portion of ApoA1, or ApoA1 mimetic, that is capable of binding HDL, and ii) an affinity tag; and b) a population of non-tagged, wild-type, ApoA1 molecules; wherein said ratio of said HDL tagging molecules to said non-tagged molecules present in said composition is 1:2-2:1.

In particular embodiments, the composition further comprises human serum, whole blood, plasma, or a reconstituted HDL sample. In further embodiments, the human serum is non-LDL depleted human serum, whole blood, or plasma. In other embodiments, the affinity tag does not contain an unpaired electron. In additional embodiments, the non-tagged, wild-type, ApoA1 molecules are part of HDL molecules.

In some embodiments, provided herein are compositions comprising: a) non-LDL depleted blood, plasma, or serum sample; and b) a population of HDL tagging molecules, each comprising: i) an HDL lipophilic core binding peptide, and ii) an affinity tag. In certain embodiments, the HDL lipophilic core binding peptide comprises an HDL binding region of Apolipoprotein A-I (ApoA1), and wherein said non-LDL depleted blood, plasma, or serum sample comprises non-tagged ApoA1 molecules. In additional embodiments, the HDL tagging molecules are present in said non-LDL depleted blood, plasma, or serum sample such that the ratio of said HDL tagging molecules to said non-tagged ApoA1 molecules is 1:2-2:1 in said composition.

In some embodiments, provided herein are compositions comprising an HDL tagging molecule comprising: a) an HDL lipophilic core binding peptide, and b) an affinity tag, wherein the affinity tag does not contain an unpaired electron.

In particular embodiments, provided herein are compositions comprising a tagged HDL molecule, wherein the tagged HDL molecule comprises: a) an HDL molecule comprising: i) an HDL lipophilic core and ii) a plurality of HDL lipoproteins, and b) an HDL tagging molecule comprising: i) an HDL lipophilic core binding peptide and ii) an affinity tag, wherein the affinity tag does not contain an unpaired electron, and wherein the HDL lipophilic core binding peptide is bound to the HDL lipophilic core.

In further embodiments, provided herein are compositions comprising: a) an HDL tagging molecule comprising: i) an HDL lipophilic core binding peptide, and ii) an affinity tag; and b) a population of capture molecules, wherein the capture molecules are specific for the affinity tag.

In certain embodiments, provided herein are kits and systems comprising: a) an HDL tagging molecule comprising: i) an HDL lipophilic core binding peptide, and ii) an affinity tag; and b) a population of capture molecules, wherein the capture molecules are specific for the affinity tag. In certain embodiments, the HDL tagging molecule is in a first container, and wherein the population of capture molecule are in a second container.

In certain embodiments, the HDL lipophilic core binding peptide comprises an HDL binding region of Apolipoprotein A-I (ApoA1). In certain embodiments, the lipophilic core binding peptide comprises a portion of human ApoA1, such as amino acid residues 188-243 of human ApoA1. In other embodiments, the plurality of HDL lipoproteins in each of the HDL molecules comprises a first and second native ApoA1 protein, and wherein at least one of the HDL tagging molecules replaces (or binds to the lipophilic core along with the first and second native ApoA1 molecules) the first native ApoA1 protein in each of the HDL molecules when the tagged HDL molecules bind to the HDL molecules. In further embodiments, the HDL lipophilic core binding peptide comprises at least a portion of ApoA1 or ApoA1 mimetic.

In further embodiments, the HDL lipophilic core binding peptide comprises an HDL binding region of Apolipoprotein A-II (ApoA2) (e.g., human ApoA1). In additional embodiments, the HDL lipophilic core binding peptide comprises at least a portion of ApoA2 or ApoA2 mimetic. In certain embodiments, the HDL lipophilic core binding peptide comprises an HDL binding region of Apolipoprotein E (ApoE) (e.g., human ApoE). In additional embodiments, the HDL lipophilic core binding peptide comprises at least a portion of ApoE or ApoE mimetic.

In particular embodiments, the affinity tag does not contain an unpaired electron (e.g., the affinity tag cannot serve as a spin label). In other embodiments, the affinity tag comprises a peptide tag selected from the group consisting of: AviTag, Calmodulin-tag, polyglutamate tag, FLAG-tag, HA-tag, His-tag, Myc-tag, S-tag, SBP-tag, Softag 1, Softag 3, Strep-tag, TC tag, V5 tag, Xpress tag, Isopeptag, and SpyTag. In certain embodiments, the affinity tag is a tag based on click chemistry. In additional embodiments, the capture molecules are selected from the group consisting of: an antibody, streptavidin, calmodulin, a nickel chelate, and a cobalt chelate. In further embodiments, the capture molecules are bound to a solid support. In additional embodiments, the solid support is selected from beads, an affinity column, a slide, or other useful solid support.

In certain embodiments, the initial sample is a blood sample, a serum sample, a plasma sample, or other biological fluid (e.g., urine). In particular embodiments, the initial same is from a mammal (e.g., dog, cat, horse, pig, or other livestock). In certain embodiments, the initial sample is from a human (e.g., a human at risk for, or with, cardiovascular disease). In certain embodiments, the initial sample is depleted of LDL particles.

In certain embodiments, at least 90% of all the proteins in the purified sample are the HDL lipoproteins (e.g., at least 90% . . . 94% . . . 98% . . . 99% . . . or at least 99.9%). In some embodiments, less than 10% of all the proteins in the purified sample are non-HDL lipoproteins (e.g., less than 10% . . . 5% . . . 1% . . . 0.2%). In certain embodiments, the non-HDL lipoproteins are primarily or completely serum albumin. In other embodiments, the method generates the purified sample from the initial sample in 1 hour or less (e.g., 1 hour . . . 45 minutes . . . 37 minutes . . . 30 minutes . . . 21 minutes . . . 15 minutes . . . or 10 minutes).

In certain embodiment, the methods further comprise assaying the purified sample in order to determine at least one characteristic of the population of tagged HDL molecules. In particular embodiments, the at least one characteristic comprises the level of cholesterol present in the population of tagged HDL molecules. In other embodiments, wherein the tagged HDL molecules comprise at least one native ApoA1 protein, and wherein the at least one characteristic comprises determining oxidation status of the native ApoA1 protein. In particular embodiments, the oxidation status of the native ApoA1 protein is determined (e.g., at one of the following tyrosine amino acid residues in the native ApoA1 protein: 29, 166, 192, and 236). In further embodiments, the assaying is performed with a technique selected from the group consisting of: mass spectrometry (MS), chromatography, LC-MS, plasmon resonance, and an assay comprising the use of polyvinyl sulfonic acid (PVS) and polyethylene-glycol-methyl ether (PEGME). In certain embodiments, the native ApoA1 from the isolated HDL molecules is quantitated (e.g. by mass spectrometry).

In certain embodiments, the at least one characteristic of the population of tagged HDL molecules is a cardiovascular disease risk marker for the subject and is used for diagnosis and/or treatment of cardiovascular disease in the subject. In particular embodiments, the cardiovascular disease marker comprises HDL-c levels in the subject. In further embodiments, the treatment comprises administering the subject a cardiovascular related therapeutic (e.g., a statin, an ACE inhibitor, an aldosterone inhibitor, an angiotensin II receptor blocker, a beta-blocker, a calcium channel blockers, a cholesterol-lowering drug, Digoxin, a Diuretic, potassium, magnesium, a vasodilator, or Warfarin) or a recommendation of a life style change.

In certain embodiments, provided herein are methods comprising: subjecting a sample comprising substantially purified non-fragmented ApoA1 proteins to mass spectrometry such that a mass spectrum report (e.g., electronic report, paper report, etc.) is generated for the non-fragmented ApoA1 proteins.

In certain embodiments, the mass spectrometry is performed at a resolution of at least 5000 full width at half maximum (FWHM) (e.g., at least 5000 . . . 6000 . . . 10,000 . . . 15,000 . . . 25,000 . . . 30,000 . . . 35,000 or higher). In some embodiments, at least a portion of the non-fragmented ApoA1 proteins comprise at least one modified amino acid that is related to increased cardiovascular disease risk (e.g., at least one, two, three, four, or more modified amino acids). In certain embodiments, the spectrum report comprises a spectrum for the portion of the non-fragmented ApoA1 proteins that comprises at least one modified amino acid. In further embodiments, the modified amino acids are selected from the group consisting of: modified tyrosines, modified tyrptophans, and modified methionines. In other embodiments, the modified tyrosines are at a position within ApoA1 selected from the group consisting of: 29, 166, 192, and 236. In particular embodiments, the modified methionines are at a position within ApoA1 selected from the group consisting of: 86, 112, and 148. In certain embodiments, the sample is from a subject, and wherein the method further comprises at least one of the following actions: i) informing the subject or the subject's physician that the subject is at increased risk for cardiovascular disease (CVD); ii) providing the mass spectrum report to the subject or the subject's physician; iii) recommending, prescribing, or administering a CVD-related therapeutic to the subject; and iv) recommending, prescribing, or administering a follow-up test to the subject related to detecting CVD risk.

In certain embodiments, provided herein are methods comprising: a) subjecting a purified HDL sample to chromatography such that a purified ApoA1 sample is generated that is substantially free of HDL-associated phospholipids, wherein the purified HDL sample comprises HDL molecules, and wherein the purified ApoA1 sample comprises non-fragmented ApoA1 proteins; and b) subjecting the purified ApoA1 sample to mass spectrometry such that a mass spectrum report is generated for the non-fragmented ApoA1 proteins.

In further embodiments, the purified HDL is generated with a method described herein (e.g., using HDL tagging molecules). In further embodiments, the HDL molecules comprise: i) the non-fragmented ApoA1 proteins, and ii) an HDL tagging molecule, wherein the HDL tagging molecule comprises: A) an HDL lipophilic core binding peptide, and B) an affinity tag. In further embodiments, the subjecting in step a) and the subjecting in step b) are accomplished by injecting the purified HDL sample into a device the performs both chromatography and mass spectrometry. In some embodiments, the device is a liquid chromatography-mass spectrometry (LC/MS) machine. In additional embodiments, the mass spectrometry is performed at a resolution of at least 5000 full width at half maximum (FWHM).

In additional embodiments, at least a portion of the non-fragmented ApoA1 proteins comprise at least one modified amino acid that is related to increased cardiovascular disease risk. In other embodiments, the max spectrum report comprises a spectrum for the portion of the non-fragmented ApoA1 proteins that comprises at least one modified amino acid. In other embodiments, the modified amino acids are selected from the group consisting of: modified tyrosines, modified tyrptophans, and modified methionines. In additional embodiments, the modified tyrosines are at a position within ApoA1 selected from the group consisting of: 29, 166, 192, and 236. In further embodiments, the modified methionines are at a position within ApoA1 selected from the group consisting of: 86, 112, and 148. In other embodiments, the sample is from a subject, and wherein the method further comprises at least one of the following actions: i) informing the subject or the subject's physician that the subject is at increased risk for cardiovascular disease (CVD); ii) providing the mass spectrum report to the subject or the subject's physician; iii) recommending, prescribing, or administering a CVD-related therapeutic to the subject; and iv) recommending, prescribing, or administering a follow-up test to the subject related to detecting CVD risk.

In some embodiments, a system comprising: a) a device comprising a mass spectrometer; and b) a purified HDL sample comprising HDL molecules, wherein the HDL molecules comprise: i) non-fragmented ApoA1 proteins, and ii) HDL tagging molecules that each comprise: i) an HDL lipophilic core binding peptide, and ii) an affinity tag.

In certain embodiments, provided herein are methods comprising: a) mixing an initial sample containing a population of HDL molecules and non-HDL biomolecules with a population of detectably labeled ApoA1 molecules to generate a mixed sample, wherein said HDL molecules each comprise: i) an HDL lipophilic core and ii) a plurality of native ApoA1 proteins, and wherein said detectably labeled ApoA1 molecules are selected from: an ApoA1 protein, an ApoA1 protein fragment, an ApoA1 protein variant, and ApoA1 mimetic; b) incubating said mixed sample such that at least some of said ApoA1 molecules bind to at least some of said HDL molecules thereby generating a population of labeled HDL molecules; c) purifying at least a portion of said population of tagged HDL molecules away from said non-HDL biomolecules to generate a purified sample comprising said labeled HDL molecules; and d) analyzing said purified sample in order to determine the ratio of detectably labeled ApoA1 molecules to said native ApoA1 proteins. In certain embodiments, said ratio is employed to determine the reverse cholesterol transport ability of the HDL in the sample.

In certain embodiments, the detectably labeled ApoA1 molecules comprise radioactively labeled atoms. In other embodiments, the detectably labeled ApoA1 molecules comprise a detectable label. In further embodiments, the detectable label is selected from: a fluorescent label, an affinity tag, a chemiluminescent label, an antibody label, or an enzyme label. In further embodiments, analyzing said purified sample is performed with a method comprising mass spectrometry.

In certain embodiments, the amount of HDL captured via the affinity tag purification methods described herein is compared to the total amount of HDL in the initial sample in order to determine a ratio which is used as a proxy for the reverse cholesterol transport ability of HDL in the sample. Determination of total HDL can be performed by measuring HDL cholesterol, which is commonly performed using "homogenous" assays which use selected reagents added in specific order to "clear" the serum sample of LDL cholesterol particles containing the lipoprotein ApoB. Subsequently, the HDL cholesterol is chemically determined using traditional enzyme coupled assays. Measuring total HDL can also be performed utilizing physical methods of HDL particle isolation, typically ultracentrifugation (e.g., Warnick et al., Clinical Chemistry September 2001 vol. 47 no. 9 1579-1596, herein incorporated by reference).

In some embodiments, the amount of native ApoA1 captured via the affinity tag purification methods described herein is compared to the total amount of native ApoA1 in the initial sample in order to determine a ratio which is used as a proxy for reverse cholesterol transport ability of HDL in the sample. ApoA1 is the primary lipoprotein component of each HDL particle. While determination of HDL cholesterol, rather than ApoA1, has been a mainstay of cardiovascular risk assessment this view is changing as the determination of ApoA1 has utility in identification of subclinical atherosclerosis (Florvall et al., Journal of Gerontology: BIOLOGICAL SCIENCES 2006, Vol. 61A, No. 12, 1262-1266, herein incorporated by reference). Total ApoA1 is typically measured using widely available immunoassay platform assays.

DESCRIPTION OF THE FIGURES

FIG. 4A shows the theoretical resolution of the native and oxidized forms of ApoA1 for the +35 charge state (+H adduct) using a mass spectrometer operated at a nominal resolution of 1000. The overlap of signal between the two forms due to insufficient resolution is indicated. FIG. 4B show the theoretical resolution of the native and oxidized forms of ApoA1 for the +35 charge state (+H adduct) using a mass spectrometer operated at a nominal resolution of 2000. The overlap of signal between the two forms due to insufficient resolution is indicated. FIG. 4C shows the theoretical resolution of the native and oxidized forms of ApoA1 for the +35 charge state (+H adduct) using a mass spectrometer operated at a nominal resolution of 10000. In this example, the peaks are fully resolved from one another.

DEFINITIONS

Figure 1A:
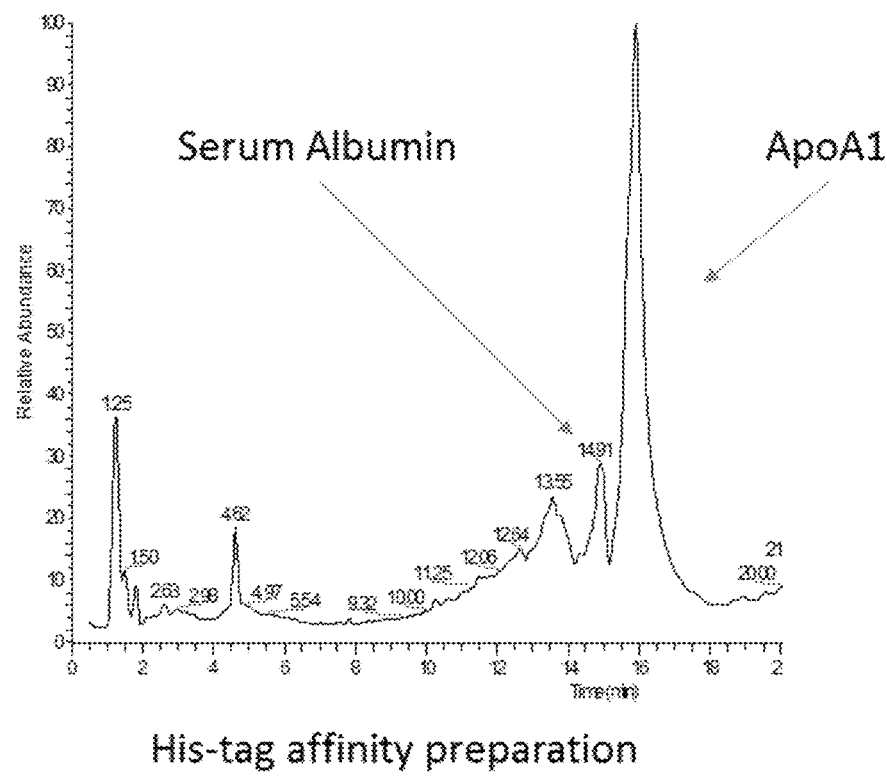
FIG. 1A shows the abundance of ApoA1 (the primary HDL associated protein), and serum albumin, when isolated by the method in Example 1.

As used herein, "high density lipoprotein" or "HDL" is a circulating, non-covalent assembly of amphipathic proteins that enable lipids like cholesterol and triglycerides to be transported within the water-based bloodstream. HDL is composed of about 50% by mass amphipathic proteins that stabilize lipid emulsions composed of a phospholipid monolayer (about 25%) embedded with free cholesterol (about 4%) and a core of triglycerides (about 3%) and cholesterol esters (about 12%). Subclasses of HDL include HDL2 and HDL3. HDL2 particles are larger and contain a higher content of lipid whereas HDL3 particles are smaller and contain less lipid. Further subclasses include from largest particle to smallest particle, HDL2b, HDL2a, HDL3a, HDL3b, and HDL3c.

As used herein, a "lipoprotein" refers to a type of protein to which one or more lipid molecules is attached or is capable of being attached. In some cases, a lipoprotein may be a "lipid-poor lipoprotein" in which four or fewer molecules of phospholipid are bound. As used herein, a lipoprotein includes a protein to which no lipid is attached but which can be exchanged in an HDL particle (e.g. an apolipoprotein).

As used herein, "sample" refers to a portion of a larger whole to be tested. A sample includes but is not limited to a body fluid such as blood, cerebral spinal fluid, urine, saliva, and the like.

As used herein, "blood sample" refers to refers to a whole blood sample or a plasma or serum fraction derived therefrom. In certain embodiment, a blood sample refers to a human blood sample such as whole blood or a plasma or serum fraction derived therefrom. In some embodiments, a blood sample refers to a non-human mammalian ("animal") blood sample such as whole blood or a plasma or serum fraction derived therefrom.

As used herein, the term "whole blood" refers to a blood sample that has not been fractionated and contains both cellular and fluid components.

As used herein, "plasma" refers to the fluid, non-cellular component of the whole blood. Depending on the separation method used, plasma may be completely free of cellular components, or may contain various amounts of platelets and/or a small amount of other cellular components. Because plasma includes various clotting factors such as fibrinogen, the term "plasma" is distinguished from "serum" as set forth below.

As used herein, the term "serum" refers to whole mammalian serum, such as, for example, whole human serum, whole serum derived from a test animal, whole serum derived from a pet, whole serum derived from livestock, etc. Further, as used herein, "serum" refers to blood plasma from which clotting factors (e.g., fibrinogen) have been removed.

DETAILED DESCRIPTION

The present invention provides methods, kits, and compositions for purifying HDL molecules from a sample (e.g., blood sample) using HDL tagging molecules comprising an HDL lipophilic core binding peptide (e.g., portion of ApoA1) and an affinity tag. In certain embodiments, such HDL purification is rapid (e.g., less than 1 hour) and allows a determination of at least one cardiovascular risk factor (e.g., cholesterol level, oxidation status of ApoA1, etc.). The present invention also provides methods, kits, and compositions for detecting full length ApoA1 with mass spectrometry without fragmenting the ApoA1. The present invention further provides methods, kits, and compositions for tagging HDL molecules in a sample with detectably labeled ApoA1 molecules such that the ratio of detectably labeled ApoA1 molecules to native ApoA1 proteins may be determined.

I. HDL Tagging Molecules

In certain embodiments, the present invention employs an HDL tagging molecule to add an affinity tag to an HDL molecule. HDL tagging molecules each comprises: i) an HDL lipophilic core binding peptide, and ii) an affinity tag.

A. HDL Lipophilic Core Binding Peptides

The HDL lipophilic core binding peptide component of the HDL tagging molecules may be any type of molecules that can bind to an HDL molecules (e.g., a mature HDL molecule) and that can be attached to an affinity tag. Such binding peptides may include, for example, at least the lipid binding portion of ApoA-I, ApoA-II, and ApoE.

ApoA-I is a lipoprotein that is a major component of HDL. An example of an apoA-I protein is the human apoA-I protein (e.g. accession number NM_000039.1). Other examples of a human apoA-I protein are the ApoA-1 milano protein and the apoA-Iowa protein. The term also encompasses apoA-I proteins from non-human mammals e.g. mouse, rat, rabbit, dog, pig, non-human primates and the like. Also encompassed by the term apoA-I are homologues of apoA-I. In certain embodiments, the HDL core binding peptide comprises the lipid binding portion of ApoA1.

ApoA-II is a lipoprotein that is the second most abundant component of HDL. An example of an ApoA-II protein is the human ApoA-II protein (e.g. NP_001634) protein. The term also encompasses ApoA-II proteins from non-human mammals e.g. mouse, rat, rabbit, dog, pig non-human primates and the like. In certain embodiments, the HDL binding peptide comprises the lipid binding portion of ApoAII.

ApoE refers to a lipoprotein that is involved in lipid metabolism and cholesterol transport. An example of an apoE protein is the human apoE protein (e.g. NM_000041.2) protein. There are three isoforms of the human apoE protein, ApoE2, ApoE3, ApoE4. ApoE3 is the predominant form of apoE, whereas apoE2 and apoE4 display distinct distributions among the lipoprotein particles (HDL, LDL, VLDL). The term also encompasses apoE proteins from non-human mammals e.g. mouse, rat, rabbit, dog, pig, non-human primates and the like. In certain embodiments, the HDL binding peptide comprises the lipid binding portion of ApoE.

In certain embodiments, ApoA1 proteins, fragments, mimetics are employed in the HDL lipid binding peptides, particularly portions of ApoA1 that are able to bind HDL. HDL binding portions of ApoA1 are discussed in, for example Murphy ISRN Physiology, 2013, article ID 186365; herein incorporated by reference). ApoA1 can include a full-length human ApoA1 peptide or to a fragment or domain thereof (e.g., comprising a class A amphipathic helix). In certain embodiments, the HDL binding peptide comprises an ApoA1 mimetic or fragment thereof. An ApoA1 mimetic include, for example, natural variants of ApoA1 that are known in the art. For example, Weisgraber et al. has shown that cysteine can be substituted for arginine at position 173 in a mutant ApoA1 termed ApoA1-Milano (Weisgraber et al. (1983) *J. Biol. Chem.* 258:2508-2513, herein incorporated by reference). ApoA1 polypeptide mimetics can also include polypeptides from the ApoA1 forms and variants including, for example, apolipoprotein A-1 (Brewer et al., (1978)), apolipoprotein A-1 Milano (Weisgraber (1983)), apolipoprotein A-1 Paris (Bielicki and Oda (2002) *Biochemistry* 41:2089-2096), proapolipoprotein A-1, or any other mutant form of ApoA1 known in the art whether synthetically formed or naturally occurring.

In certain embodiments, the HDL binding region of ApoA1 comprises amino acids 1-43 of SEQ ID NO:1, or amino acids 5-38 of SEQ ID NO:1, or amino acids 1-43 of SEQ ID NO:1 except one or two amino acids are deleted or changed without destroying the HDL binding ability of such a sequence. In other embodiments, the HDL binding region of ApoA1 comprises amino acids 220-241 or 210-241 of SEQ ID NO:1, or a 223-238 of SEQ ID NO:1, or 220-241 except where one or two amino acids are deleted or changed without destroying the HDL binding ability of such a sequence. In certain embodiments, the HDL binding region of ApoA1 comprises amino acids 44-65 of SEQ ID NO:1, or amino acids 47-62 of SEQ ID NO:1, or amino acids 44-65 of SEQ ID NO:1 except one or two amino acids are deleted or changed without destroying the HDL binding ability of such a sequence. In certain embodiments, the HDL binding region of ApoA1 comprises amino acids 1-43 and 220-241 of SEQ ID NO:1, or amino acids 5-38 and 223-238 of SEQ ID NO:1, or amino acids 1-43 and 220-241 of SEQ ID NO:1 except one or two amino acids are deleted or changed without destroying the HDL binding ability of such a sequence. In particular embodiments, the HDL binding region of ApoA1 comprises amino acids 1-43 and/or 220-241 and/or 44-65 of SEQ ID NO:1, or amino acids 5-38 and/or 223-238 and/or 47-62 of SEQ ID NO:1, or such an amino acid sequence except one or two amino acids are deleted or changed without destroying the HDL binding ability of such a sequence. The various HDL binding regions of human ApoA1 (SEQ ID NO:1) are described in Frank and Marcel, 2000, J. Lipid Res., 41:853-872, and Tanaka, J. Pept. Sci., 2009, 15(1):36-42, both of which are herein incorporated by reference, specifically with reference to the sequences of ApoA1 and the HDL binding regions thereof. FIG. 1 of Frank and Marcel is also specifically incorporated by reference. This figure shows the Apoa1 sequences of baboon, dog, pig, rabbit, cow, hedgehog, mouse, rat, chicken, duck, and salmon. This figure allows one to determine the HDL binding regions in these species that correspond to 1-43, 220-241, and 44-65 of the human sequence. Such sequences are contemplated as the HDL bind region of ApoA1 in certain embodiments of the present description. One of skill in the art can employ the methods described in Frank and Marcel, Tanaka et al., and the Examples below to determine if a particular sequence of ApoA1 (e.g., with one or more amino acid changes) binds to HDL or not (e.g., by re-running such experiments with the candidate HDL binding sequence).

Amino acid changes may be made is ApoA1, ApoA2, and ApoE, or fragments thereof, that do not destroy their ability to bind HDL lipoproteins. Such variants may be identified by assaying proposed variants and testing for binding to HDL using, for example, assays as described in the Examples below. Amino acid substitutions are generally based on the relative similarity of the amino acid side-chain substituents, for example, their hydrophobicity, hydrophilicity, charge, size, and the like. An analysis of the size, shape and type of amino acid side-chain substituents reveals that arginine, lysine, and histidine are all positively charged residues; that alanine, glycine and serine are all a similar size. Therefore, based upon these considerations, arginine, lysine and histidine; alanine, glycine and serine are defined herein as biologically functional equivalents. Following the procedures noted in the published application by Alton et al. (WO83/04053; herein incorporated by reference), one can readily design and manufacture genes coding for microbial expression of polypeptides having primary conformations which differ from that herein specified in terms of the identity or location of one or more residues (e.g. substitutions, terminal and intermediate additions and deletions).

Alternately, modifications of cDNA and genomic genes may be readily accomplished by well-known site-directed mutagenesis techniques and employed to generate analogs and derivatives of ApoA1, ApoA1, and ApoE.

B. Affinity Tags

The present invention is not limited by the affinity tag that is used as part of the HDL tagging molecule. Examples of such tags include, but are not limited to, Glutathione-S-transferase (GST), Maltose binding protein (MBP), Green Fluorescent Protein (GFP), AviTag (a peptide allowing biotinylation by the enzyme BirA and so the protein can be isolated by streptavidin), Calmodulin-tag (a peptide bound by the protein calmodulin), polyglutamate tag (a peptide binding efficiently to anion-exchange resin such as Mono-Q), FLAG-tag (a peptide recognized by an antibody), HA-tag (a peptide recognized by an antibody), His tag (generally 5-10 histidines which are bound by a nickel or cobalt chelate), Myc-tag (a short peptide recognized by an antibody, S-tag, SBP-tag (a peptide which binds to streptavidin), Softag 1, Strep-tag (a peptide which binds to streptavidin or the modified streptavidin called streptactin), TC tag (a tetracysteine tag that is recognized by FlAsH and ReAsH biarsenical compounds), V5 tag, Xpress tag, Isopeptag (a peptide which binds covalently to pilin-C protein), and SpyTag (a peptide which binds covalently to SpyCatcher protein). In certain embodiments, the tags are based on click chemistry.

The affinity tag may be coupled directly to the HDL phospholipid core binding peptide, or may be separated by intervening molecules, such as linkers. In certain embodiments, a linker is employed between the HDL lipophilic core binding peptide and the affinity tag. Examples of suitable linkers include, but are not limited, PEG linkers, peptide linkers, alkyl or substituted alkyl linkers, etc. In some embodiments, affinity tag and HDL lipophilic core binding peptide are directly conjugated, tethered, fused, etc. (e.g., via covalent bond). In other embodiments, two moieties are connected by a suitable linker. The present invention is not limited to any particular linker moiety. In some embodiments, the linker connects two moieties. In some embodiments, the linker moiety covalently connects two moieties. In some embodiments, a linker moiety is cleavable (e.g., chemically cleavable, enzyme cleavable, etc.), such that exposure to appropriate conditions (e.g., cleaving enzyme) cleaves the linker moiety and separates the connected moieties. In some embodiments, the linker moiety is a covalent linkage that is: linear, branched, cyclic, heterocyclic, saturated, unsaturated, or various combinations thereof. In some embodiments, the linker comprises 1-100 non-hydrogen atoms (in addition to hydrogen atoms) selected from the group of C, N, P, O and S (e.g. 1-75, 1-50, 1-40, 1-30, 1-20, 1-10, 1-5, etc.). In some embodiments, the linker comprises any combination of alkyl, ether, thioether, polyether, amine, alkyl, amide, ester, carboxamide, sulfonamide, hydrazide bonds and aromatic or heteroaromatic bonds. In some embodiments, the linker comprises a polymer (e.g. nucleic acid, polypeptide, lipid, or polysaccharide), a peptide linker, a modified peptide linker, a Poly(ethylene glycol) (PEG) linker, a streptavidin-biotin or avidin-biotin linker, polyaminoacids (e.g., polylysine), functionalized PEG, polysaccharides, glycosaminoglycans, dendritic polymers such as described in WO93/06868 and by Tomalia et al. in Angew. Chem. Int. Ed. Engl. 29:138-175 (1990), PEG-chelant polymers such as described in W94/08629, WO94/09056 and WO96/26754, oligonucleotide linker, phospholipid derivatives, alkenyl chains, alkynyl chains, disulfide, or a suitable combination thereof. In some embodiments, a linker moiety comprises any covalent or noncovalent molecular connector capable of stably stringing together a first and second moiety.

II. Detection Techniques

The present invention is not limited by the methods used to detect HDL and/or ApoA1 (e.g., isolated with the methods described herein).

A. Detection Methods

In certain embodiments, the HDL (and associated ApoA1) isolated via the purification methods described herein are detected with a detection methods selected from the following: surface plasmon resonance, an in vitro assay, an activity assay, co-immunoprecipitation assay, mass spectrometry, Fluorescence Energy Transfer (FRET), bioluminescence energy transfer (BRET), interferometry, Biolayer Interferometry (BLI), Dual Polarization Interferometry ("DPI"), Ellipsometry, and Quartz Crystal Microbalance (see, e.g., U.S. Pat. Pub. 20130017556, herein incorporated by reference in its entirety).

B. Mass Spec Detection of Intact ApoA1

In certain embodiments, provided herein are methods for detecting intact ApoA1 protein (i.e., non-digested, full-length ApoA1) via mass spectrometry. The wild-type protein ApoA1 is encoded by a specific amino acid sequence. This sequence represents the functional protein after the removal of a 24 amino acid precursor sequence and is shown in SEQ ID NO:1 below:

(SEQ ID NO: 1)
DEPPQSPWDRVKDLATVYVDVLKDSGRDYVSQFEGSALGKQLNLKLLDNW

DSVTSTFSKLREQLGPVTQEFWDNLEKETEGLRQEMSKDLEEVKAKVQPY

LDDFQKKWQEEMELYRQKVEPLRAELQEGARQKLHELQEKLSPLGEEMRD

RARAHVDALRTHLAPYSDELRQRLAARLEALKENGGARLAEYHAKATEHL

STLSEKAKPALEDLRQGLLPVLESPKVSFLSALEEYTKKLNTQ

The mass of ApoA1 is derived from the atomic composition of ApoA1 based on the sequence. The atomic formula is $C_{1241}H_{1977}N_{347}O_{389}S_3$ which gives a nominal, average neutral mass of 28078.26 Da.

Figure 3:
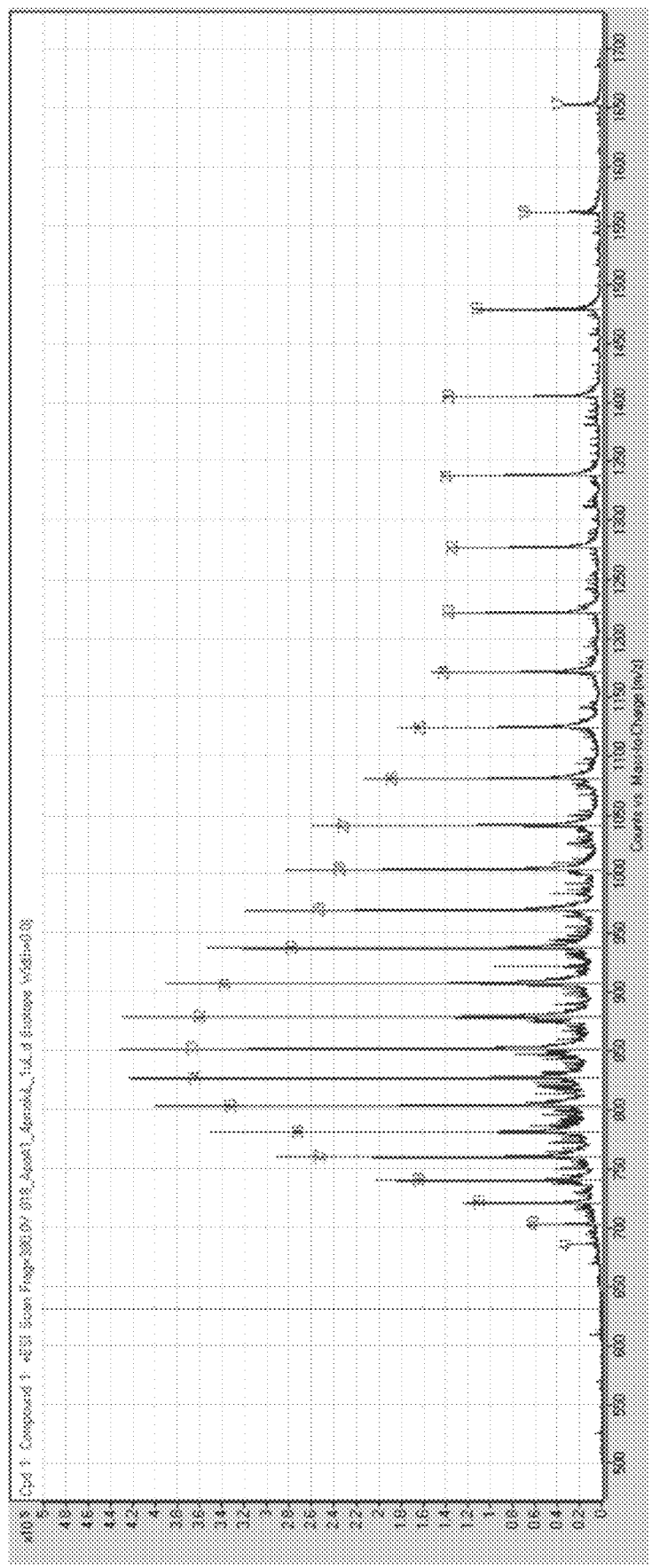
FIG. 3 shows an exemplary mass spectrometry spectrum for intact ApoA1. In this figure, charge states 32, 33, and 34 at nominal m/z values of 878, 851, and 826 respectively, provide the most intense signal.

In one exemplary embodiment, intact ApoA1 in serum or plasma can be detected by mass spectrometry by the following methods. In preparation for separation and detection by LC/MS, intact ApoA1 protein is injected onto a HPLC column under substantially aqueous conditions (e.g., 94.8% water, 5% organic, and 0.2% acid where the organic is typically methanol, acetonitrile, or isopropanol, and the acid is typically acetic or formic). By virtue of the hydrophobic nature of proteins, the ApoA1 protein binds to the column and salts and other hydrophilic contaminants are swept away under a constant flow of solvent. To resolve ApoA1 from other proteins that may be present in the sample, the composition of the solvent flow over the column is adjusted to increase the percentage of organic modifier. This change can be adjusted in a sample or complex linear gradient or series of steps such that proteins with different binding affinities can be eluted from the column at different solvent compositions. The eluent from the HPLC column can be diverted to any number of detectors (UV/Vis, light scattering, etc). For detection by LC/MS the eluate is sent to a mass spectrometer that detects molecules based on controlling the behavior of gas phase ions such that they can be resolved by their mass to charge (m/z) ratio. The first step in this process is the generation of gas phase protein ions which are typically generated by electrospray ionization. In this process, solvent is removed from the protein molecules under conditions which allow hydrogen ions to remain adducted to the protein forming a charged, gas phase ions. In an electrical field, the ions are drawn into the mass spectrometer where they are resolved by their m/z ratio. In the case of many molecules, z can have a value greater than 1 and a full scan spectrum of ApoA1 is instructive. The spectrum is complex with each peak in the spectrum corresponds to ApoA1 with the specified charge state (z) for that signal. An exemplary spectrum for intact ApoA1 is shown in FIG. 3.

In principle, any of the identified charge states can be used to quantify ApoA1 with obvious benefits/limitations. In exemplary FIG. 3, charge states 32, 33, and 34 at nominal m/z values of 878, 851, and 826 respectively provide the most intense signal for utilization in selective detection. However, in certain embodiments, the most intense signals may not always be used if there are other co-eluting molecules that interfere with those ions. The charge state distribution for a multiply charged ion can be modified depending on a number of parameters including mobile phase composition, heat and gas flows, and electrical field strength. In addition adducts other than hydrogen can also be used. For example, a sodium atom has a single positive charge but a mass of 23 Da. If ApoA1 at charge state 32 was comprised of 1 sodium and 31 proton adducts the nominal mass would be m/z 879. Therefore the addition of other ionic species to the chromatographic solvent, in certain embodiments, can be a useful way to modify the charge state distribution. Adducts that may be used, include, but are not limited to, sodium, potassium, lithium, ammonium.

Figure 4A:
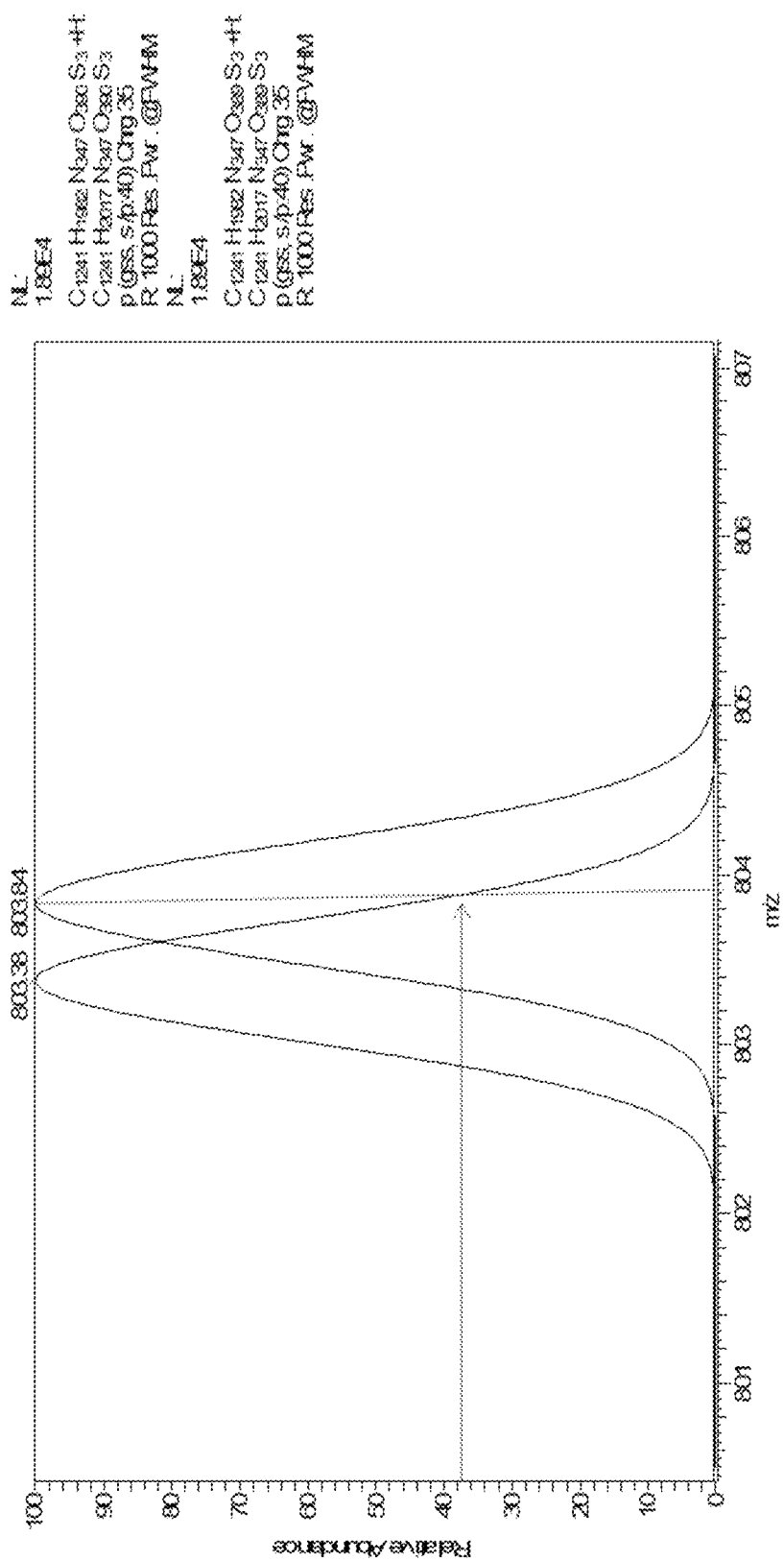
FIGS. 4A-C show the results of intact detection of ApoA1 and ApoA1 a single oxidation. In particular.
Figure 4B:
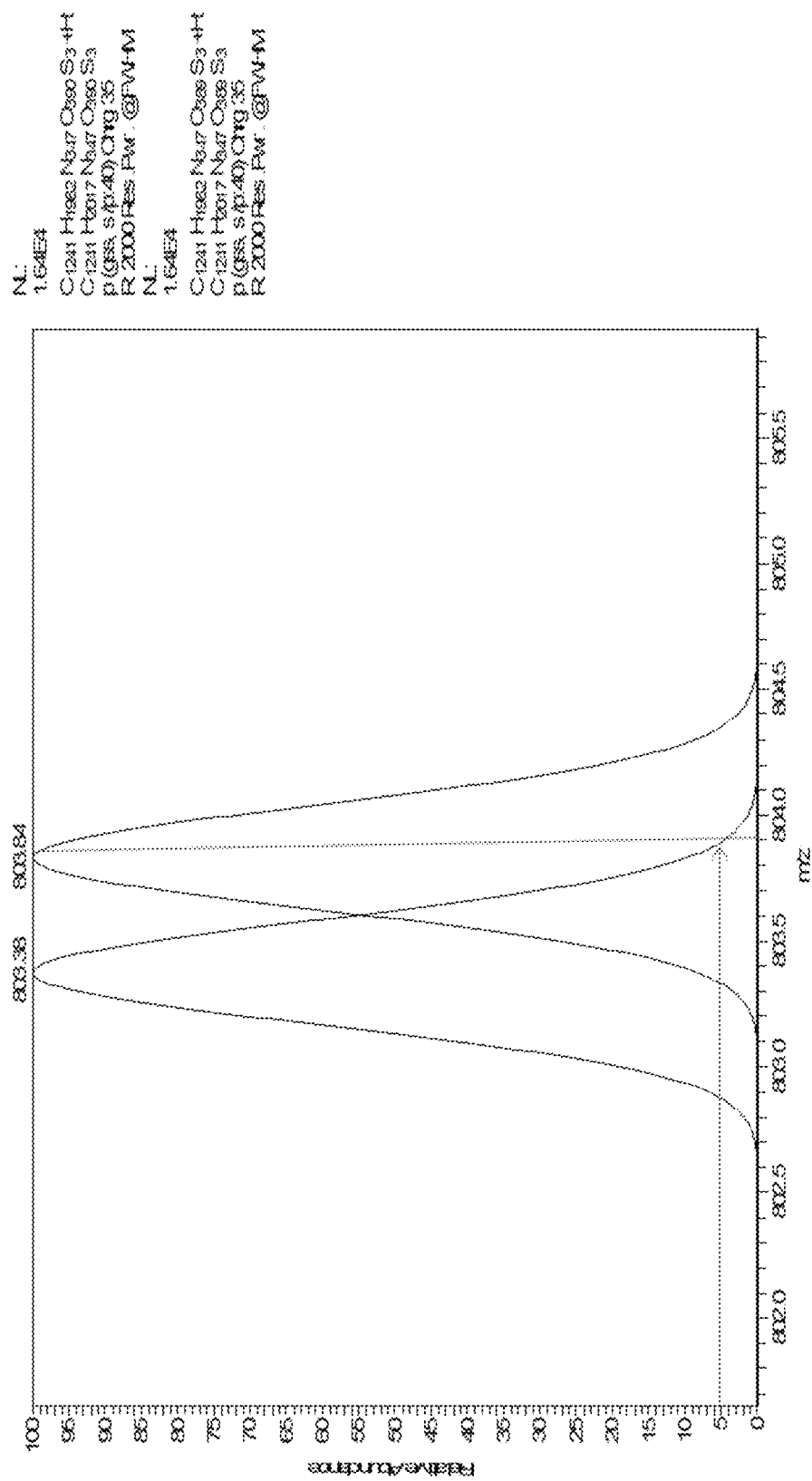
Figure 4C:
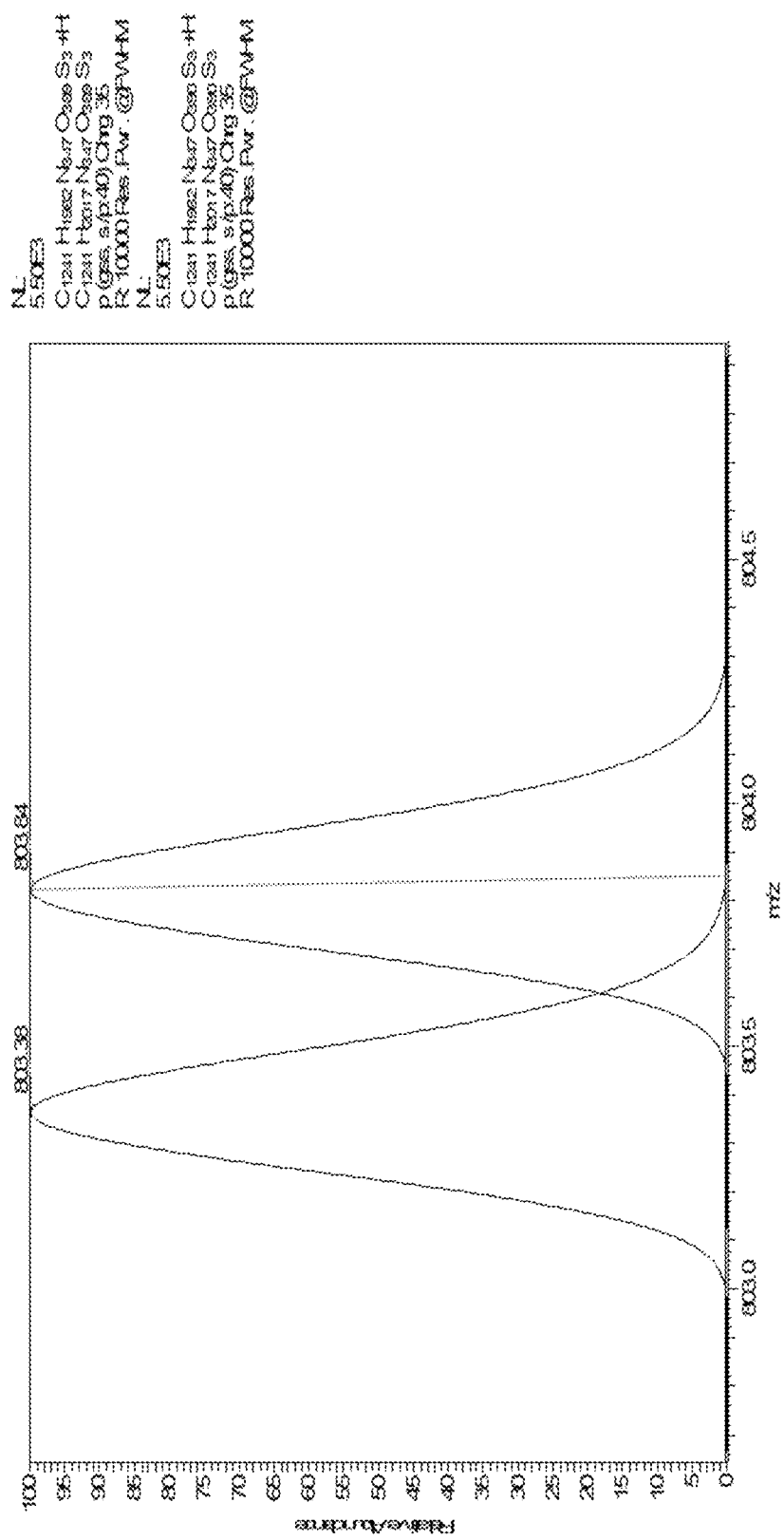
Figure 5A:
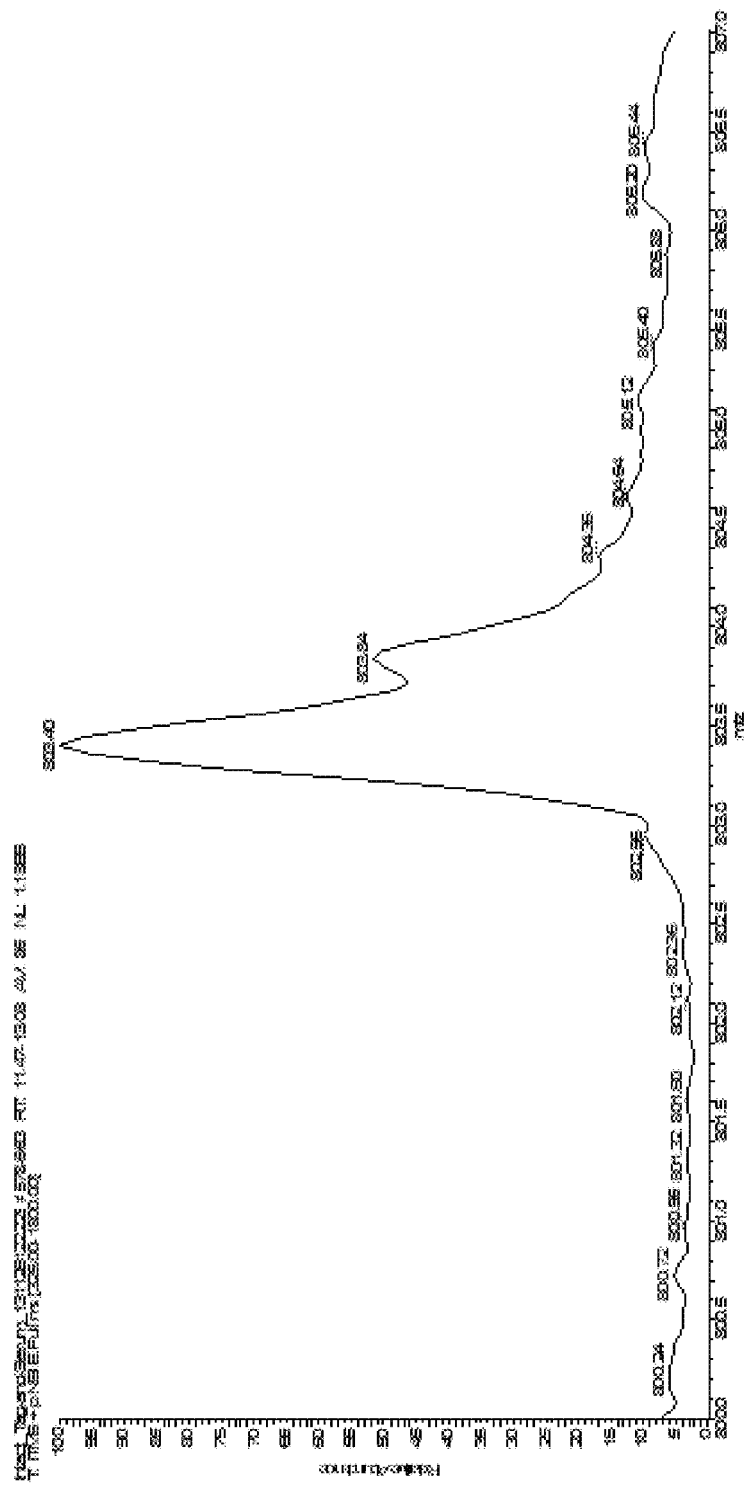
FIGS. 5A-B show data of the +35 charge state of ApoA1 and ApoA1 oxidized forms collected on a low resolution ion trap (top panel, FIG. 5A) operated at a nominal resolution of approximately 2500 FWHM, while the bottom panel (FIG. 5B) shows the same sample collected of a qTOF instrument operation at a nominal resolution of >30,000 FWHM.
Figure 5B:
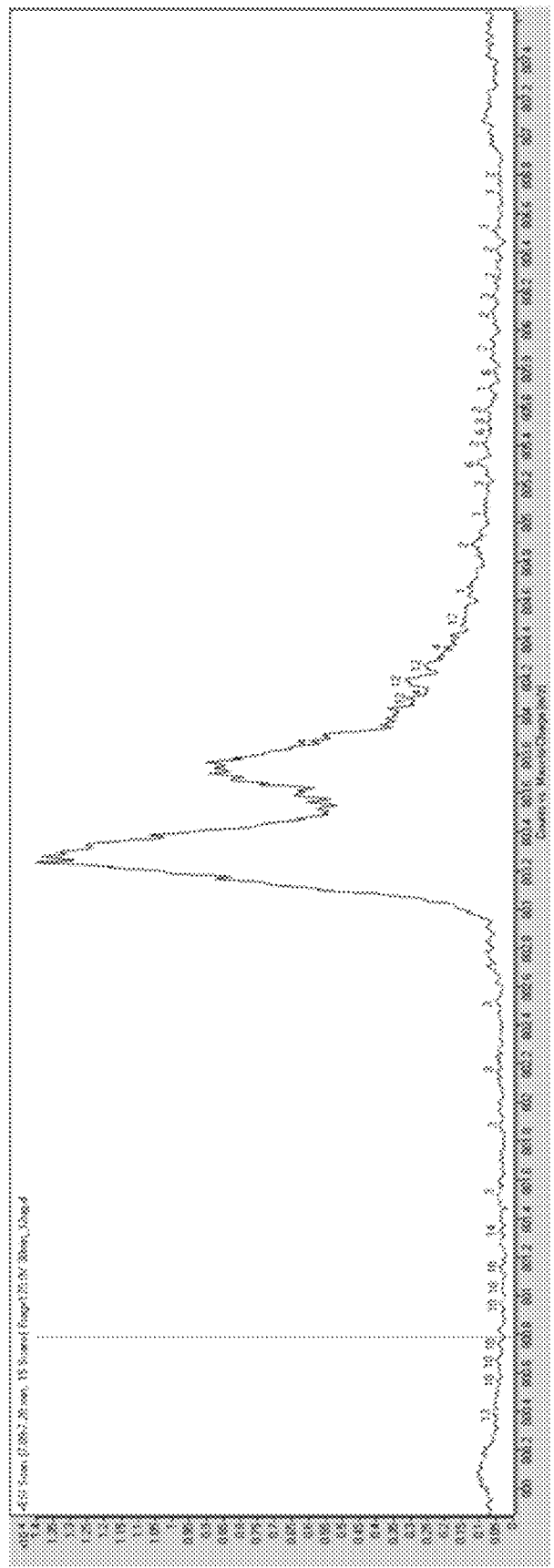

Mass spectrometry detection of intact ApoA1 may be used to identify modified (e.g., oxidized) versions of ApoA1. In certain embodiments, the modifications are relevant to cardiovascular disease detection and risk assessment. Such modifications that can be detected include modified methionines (e.g., which are sensitive to sulfone formation), tryptophan oxidation, and tyrosine modification (e.g., tyrosine chlorination, nitration, or bromination). The most relevant positions in ApoA1 for detecting the risk of cardiovascular disease with regard to tyrosines are positions 29, 166, 192, and 236 (see, e.g., U.S. Pat. No. 8,338,110, herein incorporated by reference in its entirety). In regard to methionines, it is known that three positions are particularly relevant (Met86, Met 112, and Met148), all of which may be oxidized making the methionines subject to conversion to the sulfoxide form (see, Pankhurst et al., J. Lipid Res., 44:349-355, 2003; Shao et al, J Lipid Res. July 2010; 51(7): 1849-1858; and Shao et al., Chem Res Toxicol. Mar. 15, 2010; 23(3): 447-454; all of which are herein incorporated by reference). In biological samples, the consequence of this process is that an ensemble of ApoA1 molecules may exist where the number of sulfoxides can range from 0-3. In cases, where it is desirable to specifically determine the amount of ApoA1, and the specific contributions from each oxidized form in the ensemble, the mass spectrometer should be capable of operation at a resolving power sufficient to discriminate each form from the other. In FIG. 4a-c, the impact on the resolving power of the mass spectrometer is demonstrated. Using ApoA1 and ApoA1 with a single oxidation at the +35 charge state (m/z 803.38 and 803.84 respectively) modeled data derived from an instrument with a resolving power of 1000, 2000 and 10000 FWHM are presented. At higher resolving powers, the isotopic contribution of a lower charge oxidation state to the higher charge state due to overlap is minimized. To achieve less than 2% contribution due to isotopic overlap, the mass spectrometer should be operated with a resolving power of 5000 FWHM or greater. The use of lower resolving instruments would generally necessitate using peak deconvolution to estimate and subsequently correct for the overlapping signals. In certain embodiments, a high resolution mass analyzer, such a TOF or Orbitrap, is employed and is preferable to using a low resolution ion trap or quadrupole. FIG. 5 shows data of the +35 charge state of ApoA1 and ApoA1 oxidized forms collected on a low resolution ion trap (top panel, FIG. 5A) operated at a nominal resolution of approximately 2500 FWHM. The bottom panel (FIG. 5B) shows the same sample collected of a qTOF instrument operation at a nominal resolution of >30,000 FWHM.

Figures 6A, 6B, 6C:
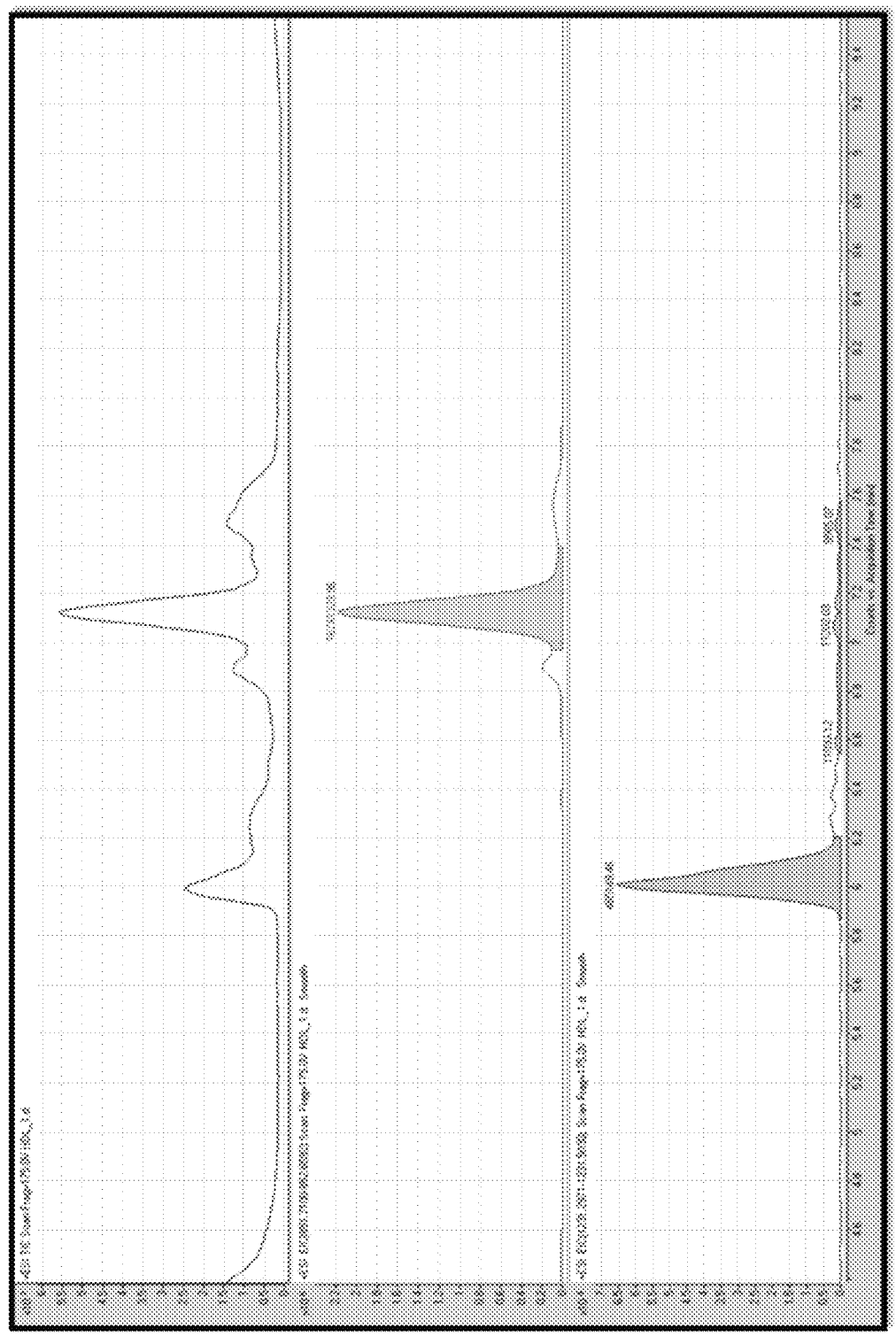
FIGS. 6A-C show how mass spectral data from a mixture of HDL proteins, specific signals for ApoA1 and serum albumin can be selectively extracted by filtering specific signals. The top panel (FIG. 6A) shows the total signal observed at the mass spectrometer over the chromatographic run. The middle panel (FIG. 6B) shows the ApoA1 signal derived by filtering data for the +35 charge state at m/z 803.38. The bottom panel (FIG. 6C) shows the contaminant serum albumin derived from the +54 charge state at m/z 1231.

Because mass spectrometry is able to resolve ions by mass, complex protein mixtures that elute at the mass spectrometer can be resolved if the resolving power and mass differences are sufficient. Generating chromatograms that are specific for a selected mass (Extracted Ion Chromatogram—EIC) can yield chromatograms that are specific for that molecule. FIG. 6 shows how mass spectral data from a mixture of HDL proteins, specific signals for ApoA1 and serum albumin can be selectively extracted by filtering specific signals. The top panel (FIG. 6A) shows the total signal observed at the mass spectrometer over the chromatographic run. The middle panel (FIG. 6B) shows the ApoA1 signal derived by filtering data for the +35 charge state at m/z 803.38. The bottom panel (FIG. 6C) shows the contaminant serum albumin derived from the +54 charge state at m/z 1231.

III. HLD, ApoA1, and Cardiovascular Disease Association

In certain embodiments, the mass spectrometry detection of intact ApoA1 (e.g., modified ApoA1) and/or the HDL purification protocols described herein, are employed to detect cardiovascular disease (CVD) or the risk of CVD in a patient by testing a patient sample with such methods.

For example, in certain embodiments, the methods may be used to determine the ability of HDL to support reverse cholesterol transport. Reverse cholesterol transport (RCT) is one pathway for removing excessive cholesterol from extrahepatic cells and tissues and eventual transport to the liver for excretion thus reducing the accumulation of cholesterol in arteries. Assessment of RCT is valuable, for example, for estimating overall cardiovascular risk and evaluating the efficiency of possible therapy aimed at boosting RCT. While the present invention is not limited to any particular mechanism, it is believed that the degree of ApoA1 exchange (e.g., when adding tagged or otherwise labeled ApoA1 to a patient sample containing HDL) is directly related to its lipid efflux and carrying capacity. Therefore, in certain embodiments, free ApoA1 (e.g., affinity tagged ApoA1) is added to a system and then assays are employed to determine how much of the added ApoA1 ends up associated with HDL particles.

One exemplary embodiment for making such an assessment is as follows. First, mix serum containing HDL with labeled ApoA1 such that endogenous ApoA1 can be identified from the labeled ApoA1. The label could be incorporated, for example, via isotope incorporation, addition of a unique affinity tag, addition of extra amino acids, or chemical modification of the ApoA1 to be added. After the mixture equilibrates, it is expected that some proportion of the HDL now contains labeled ApoA1. In certain embodiments, an excess of labeled ApoA1 might need to be removed to facilitate the measurement of incorporation level. Therefore, ultracentrifugation or other separation technique capable of resolving HDL from the unincorporated ApoA1 is employed. Finally a measurement of the HDL if performed to determine the ratio of labeled ApoA1 to unlabeled ApoA1 using any suitable technique. In such methods, a high level of ApoA1 incorporation indicates that the HDL molecules have a high level of reverse transport capacity (generally good for cardiovascular disease health), and that HDL molecules with a low level of reverse transport capacity show an increased risk for cardiovascular disease.

A second exemplary embodiment is as follows. First, mix serum containing HDL with labeled ApoA1 such that the endogenous ApoA1 can be identified from the labeled ApoA1 and the label can be used to facilitate separation (e.g., an affinity tag is used as the label). After the mixture equilibrates, a proportion of the HDL will now contain a labeled ApoA1. An affinity resin is then used to isolate all of the labeled ApoA1 and whatever portion of endogenous ApoA1 comes along via incorporation of the tag into the HDL particles. Finally a measurement of the HDL to determine the ratio of labeled ApoA1 to unlabeled ApoA1 is performed using any suitable technique. In this case, the amount of unlabeled ApoA1 is the important value as it arises based on the degree of incorporation. One could also determine the ratio of captured HDL to total available HDL.

In certain embodiments, the oxidation of ApoA1 is analyzed to assess CVD disease risk. Oxidized ApoA1 have reduced cholesterol efflux stimulating activity as compared to un-oxidized ApoA1. Therefore, detecting elevated levels of oxidized ApoA1 in patient sample with the compositions and methods described herein can be used to determine that a subject is at risk of having cardiovascular disease (see, e.g., U.S. Pat. No. 8,338,110, herein incorporated by reference). In certain embodiments, tyrosine residues are interrogated, including positions 29, 166, 192, and 236 (e.g., to determine if these positions are chlorinated or nitrated).

EXAMPLES

Example 1

Purification and Characterization of HDL Molecules from Sample

This Example describes methods of purifying HDL molecules using ApoA1 molecules attached to affinity tags, as well as methods of characterizing the purified HDL molecules.

Rapid Isolation of Functional HDL

Human serum was depleted of LDL particles by traditional methods. In particular, a 600 uL aliquot of human serum was mixed with 40 uL of dextran sulfate/magnesium chloride solution. The sample was vigorously agitated, incubated at room temperature for 10 minutes and the ApoB containing precipitate removed by centrifugation at 6,600×g for 10 minutes. The supernatant was decanted and used for further experiments.

To achieve HDL purification, 12 uL of ApoB depleted serum was mixed with 24 uL of affinity-tagged ApoA1 and 4 uL of PBS. The affinity tag in this example was poly histidine. The sample was vigorously mixed and incubated at 37 degrees Celsius. After incubation of the his-tagged ApoA1 with ApoB depleted serum, the sample was diluted with 500 uL of 10 mM Imidazole buffer. While the present invention is not limited by any particular mechanism, and an understanding of the mechanism is not necessary to practice the invention, it is believed that the his-tagged ApoA1 replaces one of the typically 4-7 native ApoA1 proteins on mature HDL molecules, thereby adding a tag to the mature HDL molecules. The sample was applied to a spin column containing Ni-NTA affinity media to capture the hig-tagged ApoA1 and associated HDL. The spin columns were briefly centrifuged to separate his-tagged ApoA1 and associated HDL particles. The spin column was then washed with 500 uL of 20 mM Imidizole buffer to remove non-specifically bound proteins. Finally, the bound HDL particles were eluted by addition of a 200 uL aliquot of 500 mM Imidizole buffer.

Protein Characterization

The purified HDL protein pools were analyzed by LC-MS and SDS-PAGE gel electrophoresis. For analytical separation prior to LC-MS all forms of ApoA1 (native or tagged) was performed with a Waters column (50×0.75 uM, C18) using a multiphase, linear gradient of increasing concentration of solvent B (acetonitrile+0.2% formic acid) in solvent A (water+0.2% formic acid). The HPLC eluate was directed to a Thermo Velos mass spectrometer operated in full scan mode.

Protein Identification

HDL associated proteins were determined using LC-MS/MS analysis of tryptic and Lys-c digests of isolated HDL particles. Three replicate preparations of the same serum sample using ultracentrifucation or affinity tag-purification were digested with the addition of endoproteinase Lys-C for 4 hours at 37° C. The resulting peptides were separated by nano-flow reverse phase liquid chromatography (C18 column 75 μm i.d. x 100 mm, 15 min. gradient) and detected by an LTQ-Orbitrap Elite mass spectrometer. Mass spectrometry data was searched using MaxQuant software employing the *Andromeda* search engine to produce a list of proteins present in each sample.

Protein Quantitation

ApoA1 was quantified using an ELISA assay.

PON1 Activity

Pon1 is an HDL associated protein with defined enzymatic activity. PON1 activity was determined by monitoring Arylesterase activity using phenyl acetate as a substrate according to Eckerson et al. (Am J Hum Genet. November 1983; 35(6): 1126-1138).

Cholesterol Efflux

Cholesterol efflux was assessed at Vascular Strategies. The assay determines the ability of isolated HDL to transport cholesterol out of cells via the ABCA1 transporter Results The method described allows for the rapid isolation of high purity, functional HDL particles from human serum/plasma under mild conditions.

Presence of HDL Associated Proteins

One hallmark of HDL is the protein composition of the particles. Numerous studies have demonstrated a number of distinct proteins are associated with HDL, with ApoA1 as the primary protein constituent (e.g., typically 4-7 ApoA1 proteins per HDL molecule). While the employed mass spectrometry methods were not optimized for depth of proteome coverage, the identified protein ID list (Table 1 below) is in good agreement with literature.

TABLE 1

| Protein names | Gene | Peptides | coverage [%] | weight [kDa] | PEP | Intensity | HDL Assoc |
|---|---|---|---|---|---|---|---|
| Apolipoprotein A-I | APOA1 | 23 | 68.9 | 30.777 | 0 | 1.88E+09 | ✓ 1 |
| Serum albumin | ALB | 21 | 31.9 | 69.366 | 1.00E−114 | 1.21E+08 | |
| Apolipoprotein A-II | APOA2 | 2 | 17 | 11.175 | 1.60E−08 | 7.34E+07 | ✓ 1 |
| Hemopexin | HPX | 7 | 14.1 | 51.676 | 1.95E−92 | 2.10E+07 | ✓ 1 |
| Complement C3 | C3 | 8 | 5.7 | 187.15 | 2.63E−25 | 6.43E+06 | ✓ 1 |
| Alpha-1-antitrypsin | SERPINA1 | 10 | 37.6 | 40.262 | 9.75E−105 | 5.58E+06 | ✓ 1 |
| Apolipoprotein C-I | APOC1 | 4 | 40.3 | 8.647 | 5.00E−21 | 5.40E+06 | ✓ 1 |
| Apolipoprotein C-II | APOC2 | 5 | 56.4 | 11.284 | 7.41E−26 | 3.04E+06 | ✓ 1 |
| Apolipoprotein C-III | APOC3 | 2 | 34.3 | 10.852 | 1.94E−10 | 1.76E+06 | ✓ 1 |
| Apolipoprotein D | APOD | 2 | 11.1 | 21.275 | 4.53E−31 | 1.69E+06 | ✓ 1 |
| Alpha-2-macroglobulin | A2M | 7 | 6.4 | 163.29 | 1.64E−83 | 1.52E+06 | ✓ 1 |
| Alpha-2-HS-glycoprotein | AHSG | 1 | 2.7 | 39.324 | 2.81E−07 | 1.16E+06 | ✓ 1 |
| Fibrinogen alpha chain | FGA | 2 | 5.6 | 69.756 | 0.000259 | 1.15E+06 | ✓ 1 |
| Apolipoprotein M | APOM | 2 | 21.8 | 21.253 | 2.65E−17 | 1.01E+06 | ✓ 1 |
| Clusterin | CLU | 2 | 24.4 | 9.3246 | 6.44E−11 | 9.09E+05 | ✓ 1 |
| Nucleobindin-1 | NUCB1 | 1 | 2.2 | 53.879 | 0.010874 | 8.78E+05 | |
| Kininogen-1 | KNG1 | 5 | 12.8 | 43.821 | 7.00E−14 | 7.73E+05 | ✓ 1 |
| Beta-2-glycoprotein 1 | APOH | 2 | 5.8 | 38.298 | 6.88E−05 | 6.85E+05 | ✓ 1 |
| Apolipoprotein A-IV | APOA4 | 2 | 5.6 | 45.398 | 3.88E−09 | 4.14E+05 | ✓ 1 |
| Serotransferrin | TF | 2 | 15.7 | 14.691 | 2.28E−05 | 3.64E+05 | ✓ 1 |
| Serum paraoxonase/aryle | PON1 | 1 | 2 | 39.731 | 0.019284 | 2.70E+05 | ✓ 1 |
| Vitamin D-binding protein | GC | 1 | 2.3 | 39.542 | 0.015131 | 1.56E+05 | ✓ 1 |
| Alpha-1B-glycoprotein | A1BG | 1 | 2.6 | 33.455 | 0.018014 | 1.47E+05 | ✓ 1 |
| Transthyretin | TTR | 1 | 8.8 | 15.887 | 0.01582 | 6.05E+04 | ✓ 1 |

The highly enriched composition of HDL associated proteins eluted from the affinity column demonstrates that HDL particles from serum are successfully isolated using the affinity tagged ApoA1 approach described above. Only two non-specific proteins (serum albumin and nucleobindin) were identified in the HDL preparation. Serum albumin is recognized as a ubiquitous contaminant in all serum based proteomics experiments. Nucleobindin has not been reported as an HDL associated protein and may represent a protein that has non-specific affinity for the nickel affinity resin used to capture the his-tagged ApoA1.

Purity of Rapidly Isolated HDL Particles

Figure 1B:
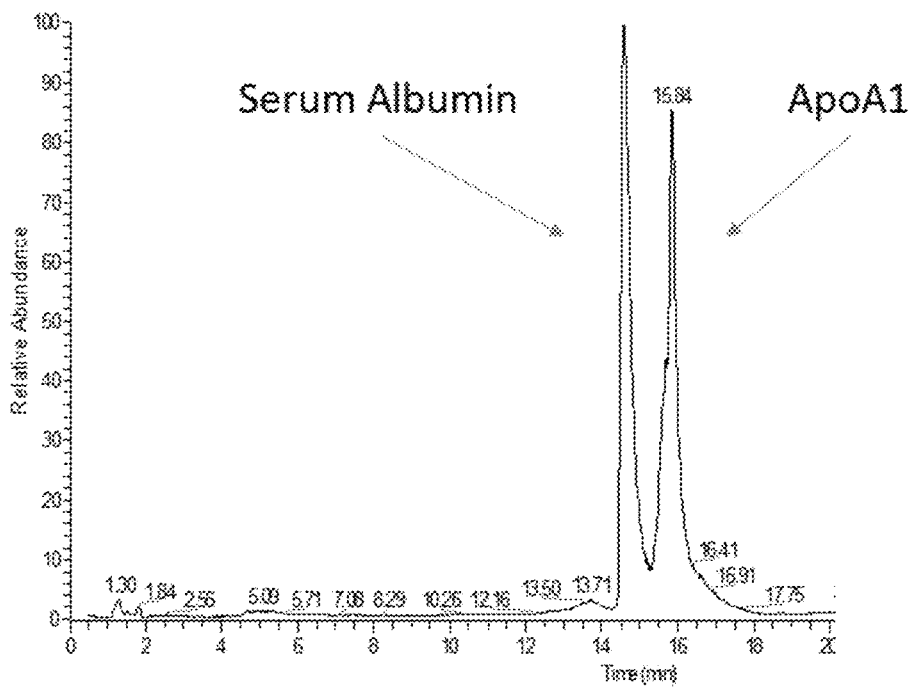
FIG. 1B shows the abundance of ApoA1 and serum albumin when ultracentrifugation is used to purify ApoA1 from serum.
Figure 2:
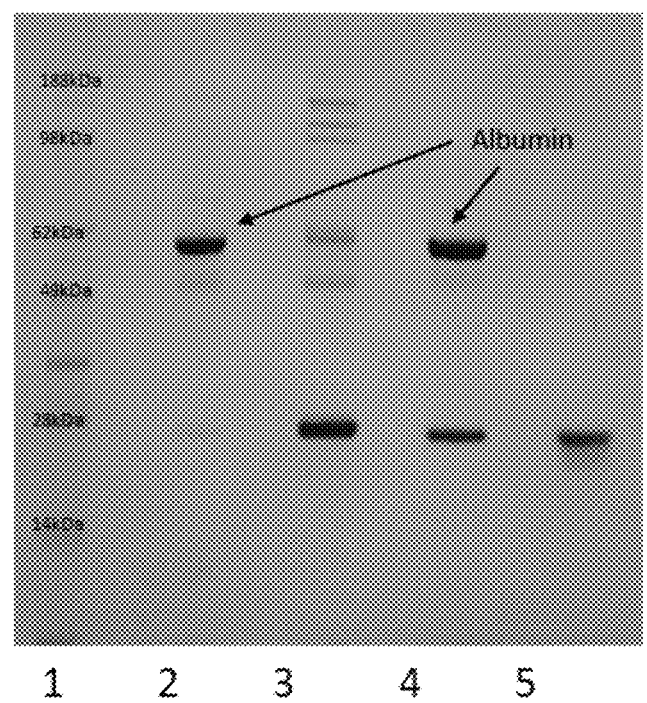
FIG. 2 shows SDS page of the various preparations from Example 1 including: 1) Ladder; 2) serum (1:50 dilution); 3) Ni-NTA HDL prep (10 ul); 4) UC HDL prep (10 ul); and 5) ApoA1 (purified from humans, 5 ug).

Both SDS page and LC-MS experiments demonstrate the purity of the rapidly isolated HDL. FIG. 1A indicates ApoA1, the primary HDL associated protein, and its relative abundance from serum when isolated by the affinity method. The purity from the affinity preparation is exemplary when compared to the gold standard ultracentrifugation preparation, which is shown in FIG. 1B. SDS page results are shown in FIG. 2. Analysis of intensity data from both LC-MS and LC-MS/MS runs indicates that the his-tag purification contains approximately 12 fold less serum albumin than a comparable ultracentrifuge preparation.

Function of Isolated HDL Particles

HDL is known to have a number of biological functions including lipid transport, cholesterol efflux, antioxidant and anti-inflammatory behavior, and endothelial activation. Paraoxonase 1 is bi-functional enzyme with both esterase and paraoxonase activity which is known to be associated with HDL. After rapid purification of HDL particles using affinity tagged ApoA1, the isolated particles were shown to have esterase activity. The particles were also show to have ABCA1 specific cholesterol efflux activity.

Exemplary Benefits of ApoA1 Affinity Tag Purification Methods

Two exemplary benefits of affinity ApoA1 purification by affinity chromatography are speed and purity. Preparation of HDL using affinity isolation can be completed in 15 minutes. For example, the serum sample is mixed with an appropriate amount of affinity tagged ApoA1 and incubated for 1-10 minutes to allow it to associate with HDL particles. After a brief equilibration (e.g., 1-2 minutes) with affinity resin (NiNTA or Co-NTA beads), the excess protein is washed away with buffer and eluted from the beads with a single application of imidazole or acid. This yields HDL with an apparent purity of >90% in 15 minutes or less.

In comparison, alternate methods for isolation of HDL are substantially more time consuming. Equilibrium ultracentrifugation of HDL from human plasma generally takes 18-24 hours but yields high quality HDL preparations which have been considered the gold standard. Size exclusion chromatography can prepare 1 sample every two hours and has been used extensively but yields diluted fractions which are associated with substantially lower purity, especially for smaller HDL sized particles.

Example 2

Purification of HDL Molecules from Neat and LDL-Depleted Serum

This Example describes the purification of HDL molecules using affinity tagged ApoA1 from LDL-depleted or neat (non-ApoB/LDL depleted) serum.

Rapid Isolation of HDL

Human serum was either depleted of LDL particles as described in Example 1 or was immediately used for rapid HDL isolation without LDL depletion. For rapid HDL purification, 12 uL of neat and LDL-depleted serum was mixed with 24 uL of $^{15}$N-labeled affinity-tagged ApoA1. In this example the affinity tag is poly histidine. The sample was briefly mixed and incubated at 37 degrees Celsius. After incubation, the sample was diluted to 700 uL with 10 mM imidazole buffer. 25 uL of Ni-NTA affinity paramagnetic beads were added to the sample and briefly incubated to bind HDL molecules incorporating the tagged-ApoA1 in addition to any additional unincorporated tag. The beads were sequentially washed twice with 300 uL of 20 mM imidazole buffer to remove non-specifically bound proteins, then eluted with 90 uL of 300 mM imidazole buffer. 10 uL of 0.5 ng/uL endoproteinase LysC was then added to the eluted HDL samples and incubated for four hours at 37 degrees Celsius to specifically cleave HDL associated proteins into specific peptides for LC-MS characterization.

Purified HDL Characterization

Peptide products from the LysC digestion of rapidly purified HDL were separated on a Phenomenex reversed-phase HPLC column (3.0×50 mm, C18) using a multiphase, linear gradient of increasing concentration of solvent B (acetonitrile+0.1% formic acid) in solvent A (water+0.1% formic acid). Eluted peptides were detected directly by an Agilent 6490 triple quadrupole mass spectrometer operating in multiple reaction monitoring mode to detect peptides specific to HDL associated proteins.

Results

Figure 7:
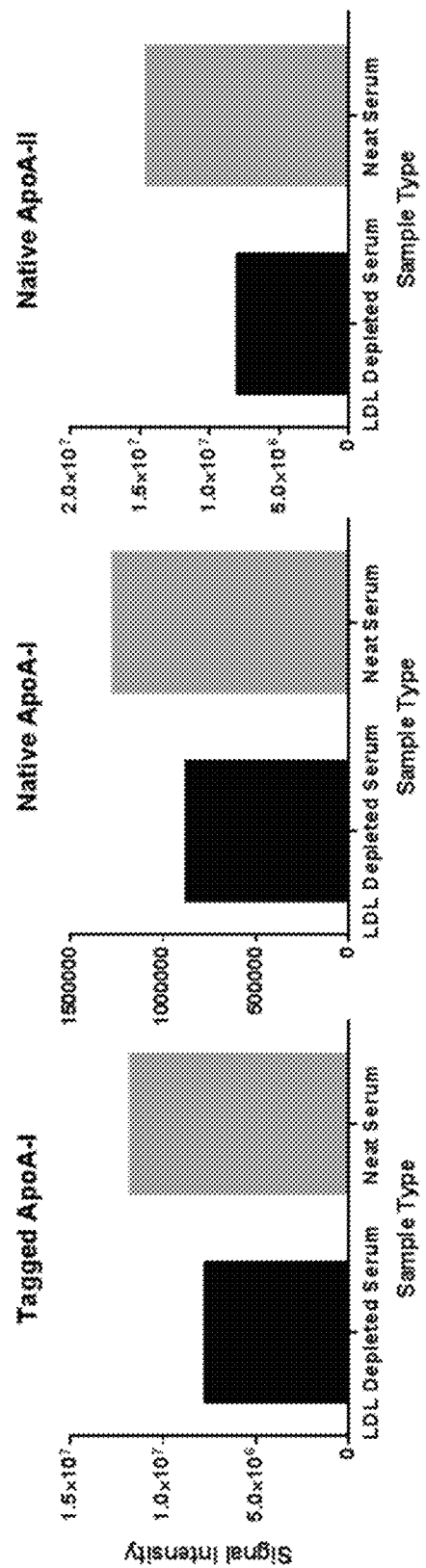
FIG. 7. Bar graphs showing the recovery of tagged ApoA1 and native HDL-associated proteins in LDL depleted/un-depleted neat serum.

Peptides specific to HDL associated proteins were detected in both neat serum and LDL-depleted serum samples in addition to tagged ApoA-I which is distinguishable by enrichment of the tagged-ApoA1 with $^{15}$N. FIG. 7 shows the intensities of Tagged ApoA1, and native, HDL specific ApoA1, and ApoA2. These results indicate the ability to rapidly isolate HDL from patient serum without the need for prior LDL-depletion.

Example 3

Optimization of Tagged ApoA1: Native ApoA1 Ratio for Rapid HDL Purification

This example describes the rapid isolation of HDL molecules with variation in the amount of tagged-ApoA1 to maximize molecule recovery.

Rapid Isolation of HDL

For rapid HDL purification, 10 uL of neat (non-LDL depleted) human serum was mixed with 24 uL of $^{15}$N-labeled affinity-tagged ApoA1 containing either 1, 2, 5, 10, 20, 40, or 80 ug of total tagged ApoA1, corresponding to a tag-to-native ApoA1 ratio of 1:10, 1:5, 1:2, 1:1, 2:1, 4:1, and 8:1, respectively. The ratio is determined based on the assumption that the mean total ApoA1 in a human serum sample is about 1 mg/mL (ug/uL). In this example the affinity tag is poly histidine. The sample was briefly mixed and incubated at 37 degrees Celsius. After incubation, the sample was diluted to 700 uL with 10 mM imidazole buffer. 25 uL of Ni-NTA affinity paramagnetic beads were added to the sample and briefly incubated to bind HDL molecules incorporating the tagged-ApoA1 in addition to any additional unincorporated tag. The beads were sequentially washed twice with 300 uL of 20 mM imidazole buffer to remove non-specifically bound proteins, then eluted with 90 uL of 300 mM imidazole buffer. 10 uL of 0.5 ng/uL endoproteinase LysC was then added to the eluted HDL samples and incubated for four hours at 37 degrees Celsius to specifically cleave HDL associated proteins into specific peptides for LC-MS characterization.

Purified HDL Characterization

Peptide products from the LysC digestion of rapidly purified HDL were separated on a Phenomenex reversed-phase HPLC column (3.0×50 mm, C18) using a multiphase, linear gradient of increasing concentration of solvent B (acetonitrile+0.1% formic acid) in solvent A (water+0.1% formic acid). Eluted peptides were detected directly by an Agilent 6490 triple quadrupole mass spectrometer operating in multiple reaction monitoring mode to detect peptides specific to HDL associated proteins.

Results

Figure 8:
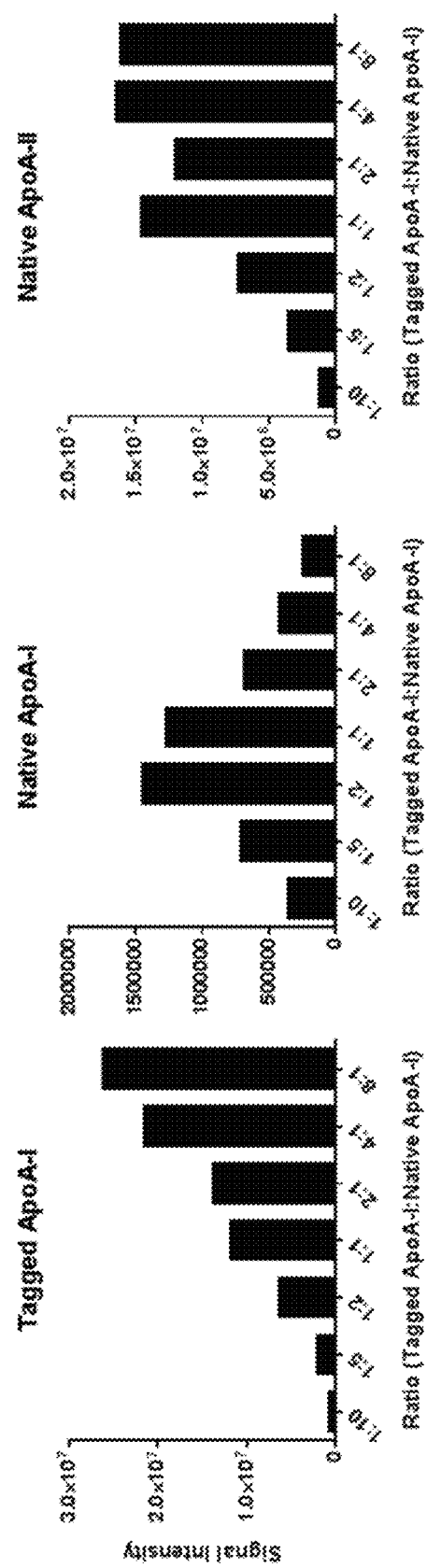
FIG. 8. Bar graphs showing the recovery of tagged ApoA1 and native HDL-associated proteins in purified HDL from serums using an increasing ratio of tagged-to-native ApoA1.

FIG. 8 shows the measured intensities of tagged ApoA1, native ApoA1, and native ApoA-II from the purified HDL molecules of identical serum samples where varying amounts of tagged ApoA1 were used to capture HDL. Tagged ApoA1 is distinguishable from native ApoA-I with the use of tagged ApoA1 isotopically labelled with $^{15}$N, producing a unique mass signature detectable by mass spectrometry. As expected, the signal intensity of tagged ApoA1 increases with the use at a greater tag-to-native ratio. As stated in Example 1, while the present invention is not limited by any particular mechanism, and an understanding of the mechanism is not necessary to practice the invention, it is believed that the his-tagged ApoA1 replaces one of the typically 4-7 native ApoA1 proteins on mature HDL molecules, thereby adding a tag to the mature HDL molecules. This is observed in the intensity of native ApoA1 in FIG. 8, as the intensity increases up to a ratio of 1:1, then decreases as tag-to-native ratio increases further. This is hypothesized to be the result of multiple ApoA1 molecules per HDL particle being replaced, displacing native ApoA1 at a greater rate. The measurement of another HDL specific protein that is not exchanged, ApoA2, serves as an indication of total HDL recovery. ApoA2 is observed to be maximized at a 1:1 ratio and plateau as the ratio of tag-to-native ApoA1 is further increased.

Example 4

Characterization of ApoA1 Tagged Purified HDL

This Example describes additional procedures used to characterize HDL isolated by the affinity tagged methods described herein.

Fatty Acid Analysis

His6-tagged ApoA-I (0.5 mg/mL) was combined with human serum at a 1:2 volumetric ratio and incubated for 15 minutes at 37 degrees Celsius. The resulting sample was diluted to 700 µL with 10 mM imidazole, 50 mM Sodium Phosphate, 300 mM Sodium Chloride, pH 8.0 and incubated 10 minutes at room temperature with paramagnetic beads containing Ni-NTA. The beads were washed twice with stripped serum and eluted with 30 µL of 300 mM imidazole. The eluted HDL was combined with 500 uL 2% Sulfuric acid in anhydrous methanol and heated at 65° C. for 1.25 hours in a sealed vial. The resulting fatty acid methyl esters were extracted into 1 mL of Heptane using a liquid-liquid extraction. The organic layer was removed and the heptane evaporated under a stream of dry nitrogen. The fatty acid methyl esters were hydrolyzed to fatty acids by the addition of sodium hydroxide and subsequently analyzed for 19 common fatty acids by LC-MS.

The following fatty acids were detected in HDL in the following proportions, C14:0, Myristic acid, 0.4%; C15:0, 0.1%, Pentadecanoic acid; C16:0, 14.%, 1.6%, Palmitic acid; C16:1, Palmitoleic acid; C18:0, Stearic acid, 10.7%; C18:1, Oleic acid, 19.7%; C18:2n6, 25.5%, Linoleic acid; C18:3, Linolenic acids. 1.2%; C20:0, Arachidic acid; C20:1, trace %, Eicosadienoic acid, 0.2%; C20:2n6, Eicosadienoic acid, 0.2%; C20:3n6, Homogamma linolenic, 4.2%; C20:4n6, 17.2%, Arachidonic acid; C22:2n6, Docosadienoic acid, 0.4%; C22:4n6, Adrenic acid, 0.5%; C22:5n6, Docosapentenoic-6 acid, 0.3%; C20:5n3 Eicosapentenoic acid 0.8%; C22:6n3 Docosahexaenoic acid, 1.9%; C22:5n3, Docosapentenoic acid, 0.6%. In the absence of tagged ApoA1, no fatty acids were detected. The composition of fatty acids detected in the HDL sample differed from the whole blood fatty acid profile showing increased proportion of unsaturated fatty acids.

miRNA Analysis

Total RNA from serum, rapidly purified HDL (using the tagged ApoA1 methods described herein) and a positive serum control was isolated using the PureLink miRNA Isolation kit (Life Technologies) and resuspended in nuclease-free water. Reverse transcription was performed using the TaqMan microRNA Reverse Transcription kit (Life Technologies). Five µL of total RNA (1-10 ng) was mixed with 1.0 mM dNTP, 3.33 U/µL Reverse Transcriptase, 1× Reverse Transcription Buffer, 0.25 U/µL RNase Inhibitor, and nuclease free water for a total of 12 ul. Three µL of the 5×RT primer was then added to the RT reaction mix for a total of 15 µL. The RT reaction was done in an Eppendorf MasterCycler pro thermal cycler according to manufacturer's directions (30 minutes, 16° C.; 30 minutes, 42° C.; 5 minutes, 85° C.; 4° C. hold). The cDNA was either stored at −15° C. to −25° C., or used immediately for quantitative analysis of miRNA.

Figure 9A:
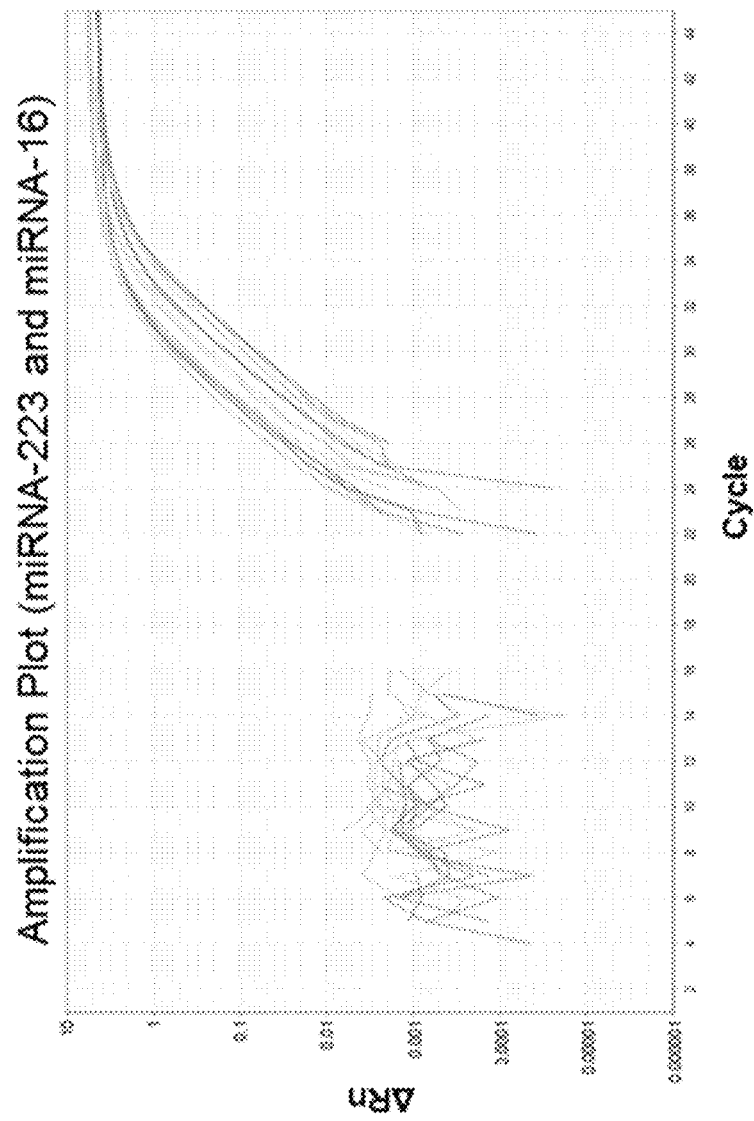
FIGS. 9A-B. A) Amplification plot showing RT-PCR of miRNA-223 and miRNA-16 (Endogenous Control) in the rapidly purified HDL of two patient samples in addition to a positive control, and B) bar graph showing relative abundances of amplified miRNA-223.
Figure 9B:
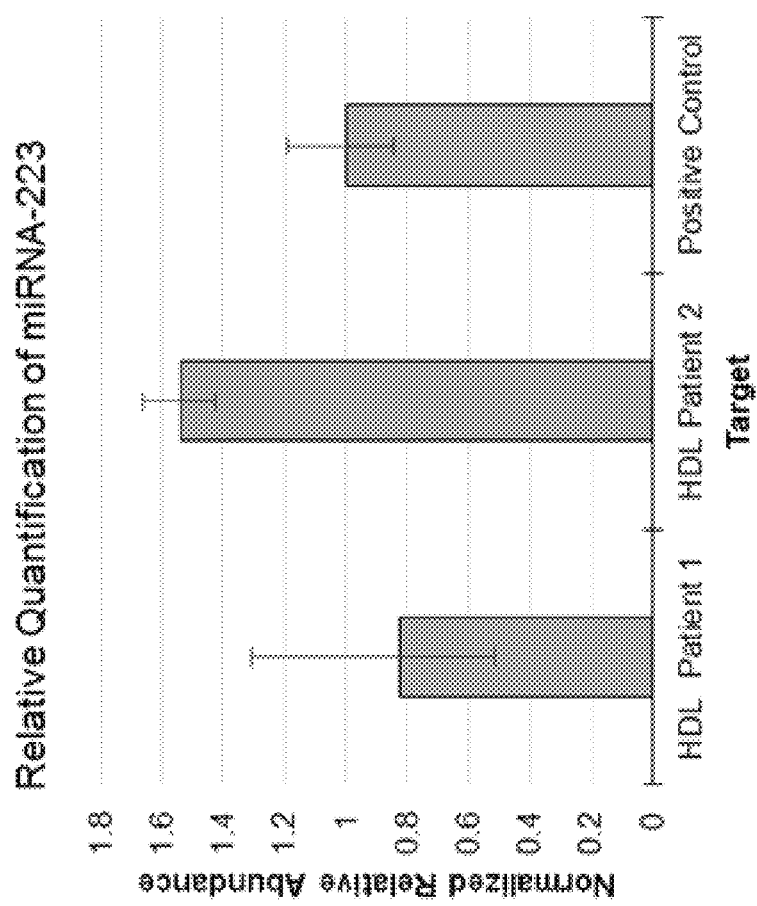

Mature miRNA-223 expression was assessed using the TaqMan microRNA single assay (assay ID002295, Life Technologies). Samples were normalized to miRNA-16 expression (assay ID000391, Life Technologies). For the PCR reaction, 1.0 ul of the TaqMan miRNA assay was mixed with 1.33 ul of the cDNA, 10 ul of the TaqMan Universal PCR Master Mix II, no UNG, and 7.67 ul of nuclease free water for a total of 20 ul in the reaction mix. All samples were run in duplicate. Real-time PCR was performed in the Life Technologies Standard 7500 Real-Time PCR System with cycling conditions of 95° C. for 10 minutes, followed by 45 cycles of 95° C. hold, 15 seconds, then 60° C. hold, 60 seconds. Comparative Ct analysis was performed to assess relative gene expression. Results, shown in FIG. 9, indicate differential miRNA-223 expression in different patient HDL samples at levels similar to those of miRNA isolated from an untreated serum sample (positive control).

Particle Size Analysis

Figure 10A:
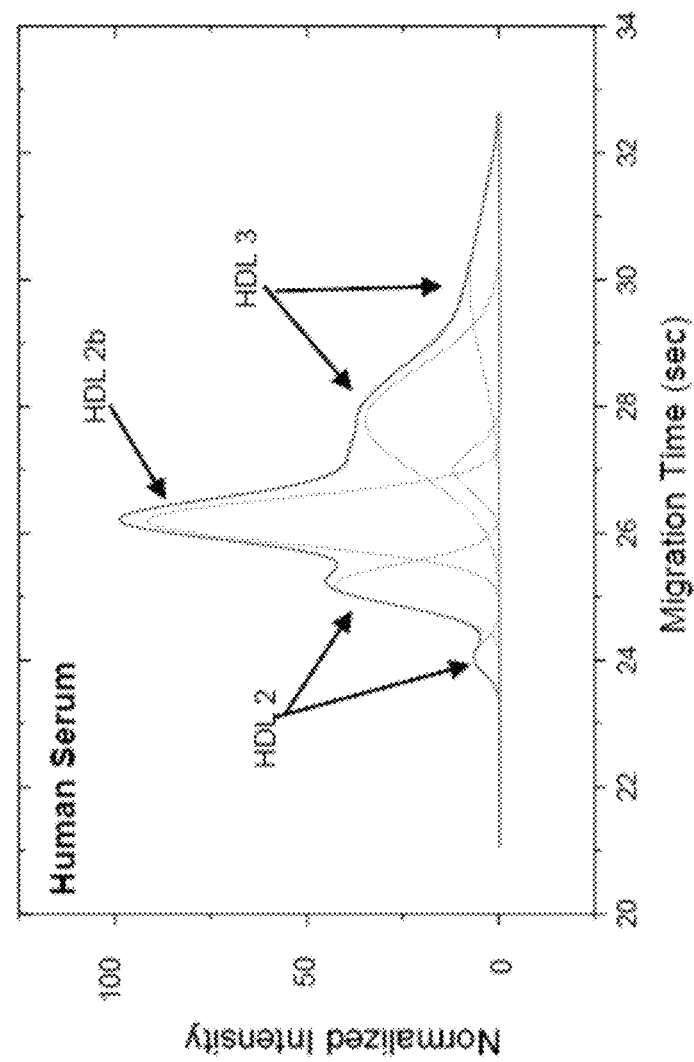
FIGS. 10A-B. Particle profile analysis of human serum (A) and rapidly purified HDL (B) from the same sample.
Figure 10B:
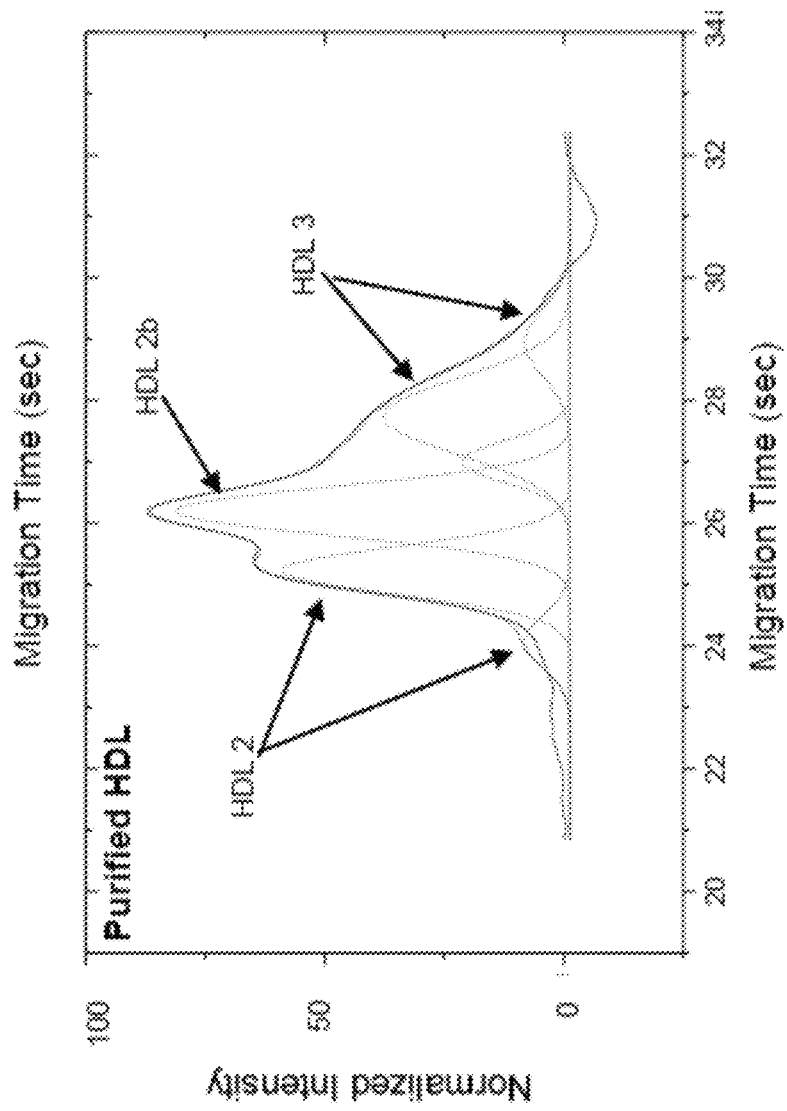

His6-tagged ApoA-I (0.5 mg/mL) was combined with human serum at a 1:2 volumetric ratio and incubated for 15 minutes at 37 degrees Celsius. The resulting sample was diluted to 700 µL with 10 mM imidazole, 50 mM Sodium Phosphate, 300 mM Sodium Chloride, pH 8.0 and incubated 10 minutes at room temperature with paramagnetic beads containing Ni-NTA. The beads were washed twice with stripped serum and eluted with 30 µL of 300 mM imidazole in stripped serum. 10 µL of eluted HDL in stripped serum was separated by microfluidic electrophoresis using an Agilent 2100 Bioanalyzer. The resulting particle profile revealed peaks corresponding to the presence of HDL2, HDL2b, and HDL3 particles in the eluted sample (FIG. 10) at similar relative abundance to the same peaks in a non-enriched serum sample.

All publications and patents mentioned in the present application are herein incorporated by reference. Various modification and variation of the described methods and compositions of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A system comprising:
    a) an HDL tagging molecule comprising:
        i) an HDL lipophilic core binding peptide comprising an HDL binding region of Apolipoprotein A-I (ApoA1), and
        ii) an affinity tag; and
    b) a population of capture molecules, wherein said capture molecules are specific for said affinity tag.

2. The system of claim 1, wherein said HDL tagging molecule is in a first container, and wherein said population of capture molecules are in a second container.

3. The system of claim 1, wherein said affinity tag comprises a peptide tag.

4. The system of claim 1, wherein said affinity tag is coupled to said region of ApoA1.

5. The system of claim 4, wherein said affinity tag is coupled to said region of ApoA1 by a linker, wherein said linker is selected from the group consisting of a PEG linker, peptide linkers and alkyl or substituted alkyl linker.

6. The system of claim 1, wherein said HDL lipophilic core binding peptide comprises at least a portion of Apolipoprotein A-I (ApoA1) or ApoA1 mimetic.

7. The system of claim 1, wherein said capture molecules are selected from the group consisting of an antibody, streptavidin, calmodulin, a nickel chelate, and a cobalt chelate.

8. The system of claim 1, wherein said captures molecules are bound to a solid support.

9. The system of claim 8, wherein said solid support is selected from the group consisting of beads, an affinity column, and a slide.

* * * * *

UNITED STATES PATENT AND TRADEMARK OFFICE
CERTIFICATE OF CORRECTION

| | |
|---|---|
| PATENT NO. | : 11,061,039 B2 |
| APPLICATION NO. | : 16/208739 |
| DATED | : July 13, 2021 |
| INVENTOR(S) | : Collier et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 34 days.

Signed and Sealed this
Thirty-first Day of January, 2023

Katherine Kelly Vidal
*Director of the United States Patent and Trademark Office*